United States Patent
Quinn et al.

[11] Patent Number: 5,772,874
[45] Date of Patent: Jun. 30, 1998

[54] HIGH PERFORMANCE LIQUID CHROMATOGRAPHY METHOD AND APPARATUS

[75] Inventors: Hubert M. Quinn, Brighton; Joseph J. Takarewski, Jr., Woburn, both of Mass.

[73] Assignee: Cohesive Technologies, Inc., Acton, Mass.

[21] Appl. No.: 661,367

[22] Filed: Jun. 11, 1996

Related U.S. Application Data

[63] Continuation-in-part of Ser. No. 552,193, Nov. 2, 1995, abandoned.

[51] Int. Cl.[6] .................................................. B01D 15/08
[52] U.S. Cl. .................................. 210/198.2; 310/502.1; 310/656
[58] Field of Search .............................. 210/198.2, 502.1, 210/635, 656, 659

[56] References Cited

U.S. PATENT DOCUMENTS

| | | | |
|---|---|---|---|
| 3,493,497 | 2/1970 | Pretorius et al. | 210/198.2 |
| 4,208,284 | 6/1980 | Pretorius | 210/198.2 |
| 4,389,385 | 6/1983 | Ramsay | 210/198.2 |
| 4,512,897 | 4/1985 | Crowder | 210/198.2 |
| 4,970,002 | 11/1990 | Ando et al. | 210/659 |
| 5,015,576 | 5/1991 | Nilsson | 210/656 |
| 5,019,270 | 5/1991 | Afeyan | 210/198.2 |
| 5,164,090 | 11/1992 | Hirth | 210/198.2 |
| 5,228,989 | 7/1993 | Afeyan et al. | 210/198.2 |
| 5,256,298 | 10/1993 | Powell | 210/660 |
| 5,268,097 | 12/1993 | Girot | 210/198.2 |
| 5,328,603 | 7/1994 | Velander | 210/198.2 |
| 5,384,042 | 1/1995 | Afeyan et al. | 210/198.2 |
| 5,387,347 | 2/1995 | Rothchild et al. | 210/659 |
| 5,401,415 | 3/1995 | Rauh | 210/198.2 |
| 5,503,933 | 4/1996 | Afeyan | 210/198.2 |

OTHER PUBLICATIONS

Snyder, Introduction to Modern Liquid Chromatography, John Wiley & Sons, 1979, pp. 173–176 and 210–216.
Guiochon, Fundamentals of Preparative and Non–Linear Chromatography, Academic Press (1984), pp. 174–176.
Kirkland, Introduction to Modern Liquid Chromatography John Wiley & Sons, 1979, pp. 234–240.
Golay, Gas Chromatography, Buttersworth, London, 1958 pp. 36–55.
Aris, Proc. Roy. Soc. A 235, 1956, pp. 67–77.
Aris, Proc. Roy. Soc A 252, 1959, pp. 538–550.
C. Giddings, Advances in the Theory of Plate Height in Gas Chromatography, *Analytical Chemistry*, vol. 35, No. 4, Apr. 1963, pp. 439–448.
Sir G. Taylor, Fluid Flow in Regions Bounded by Porous Surfaces, *Proc. Royal Soc. of London*, vol. 234A, 1956, 456–475.

(List continued on next page.)

*Primary Examiner*—Ernest G. Therkorn
*Attorney, Agent, or Firm*—Lappin & Kusmer LLP

[57] ABSTRACT

A method of and apparatus for liquid chromatography at improved analytical and preparative speeds and quantities involves flow of fluids through the column at flow rates sufficient to induce turbulent flow in those fluids. In one embodiment, the apparatus and method includes a substantially uniform chromatography column created by packing together a multiplicity of rigid, solid, porous particles having diameters of not less than about 30 μm, surfaces of the particles being chromatographically active. A fluid mixture containing at least one solute that is reactive with the particle surfaces is injected into the column and subsequently eluted therefrom by a eluant fluid flow, both the injection and elution being effected at a velocity sufficient to induce flow within at least a substantial portion of the interstitial volume between the particles at a reduced velocity greater than about 5,000.

22 Claims, 13 Drawing Sheets

OTHER PUBLICATIONS

W. Kopaciewicz et. al., High Velocity Reversed Phase Chromatograph of Proteins and Peptides; Use of Conventional C18, 300Å, 15 µm Particles, *J. Chromatog.* A, 690, 1995, 9–19.

C. Giddings,et. al., Plate Height in Gas Chromatography, *Analytical Chemistry*, vol. 32, No. 7, Jun. 1960, pp. 867–870.

*Introduction to Liquid Chromatography*, 2nd Ed., Snyder and Kirkland, John Wiley & Sons, N.Y. (1979), pp. 238–241.

V. Pretorius and T. Smuts, Turbulent Flow Chromatography: a New Approach to Faster Analysis, *Analytical Chemistry*, vol. 38, No. 2, Feb. 1966, pp. 274–280).

D.S. Horne et. al., A Comparison of Mobile–Phase Dispersion in Gas and Liquid Chromatography, *Sep. Science*, 1(5), 531–554 (1966).

H. Kaizuma et. al., Evaluation of Coupling and Turbulence by the Dynamical Comparison of Gas and Liquid Chromatography, *J. Chrom. Science*, vol. 8, 630–534 (Nov. 1970).

S. H. Sumpter, et. al., Enhanced Radial Dispersion In Open Tubular Column Chromatography, *J. Microcol.*, 3, 91–113, (1991).

H. Bauer, Open–Tubular Liquid Chromatography under Turbulent and Secondary Flow Conditions, *Chromatographia*, vol. 27, No. 5/6, 238–242, (Mar. 1989).

R. Tijssen, Liquid Chromatography in Helically Coiled Open Tubular Columns, *Sep. Science and Tech.*, 13(8), 681–721 (1978).

K. Hofmann et. al., Mass Transfer in Ideal and Geometrically Deformed Open Tubes, I. Ideal and Coiled Tubes with Circular Cross–Section, *J. Chromatogr.* 173, 211–229 (1979).

I. Halasz, Mass Transfer in Ideal and Geometrically Deformed Open Tubes–II. Potential Applications of Ideal and Coided Tubes in Liquid Chromatography., *J. Chromatogr.* 173, 229–247 (1979).

M. Martin et. al., Influence of Retention on Band Broadening in Turbulent Flow Liquid and Gas Chromatography., *Anal. Chem.*, 54, 1533–1540 (1982).

D. Dewaele et. al., Some L.C.Experiments with Capillary Columns, *J. High Res. Chromatog. and Chromatog. Commun.*, 1, 174–176 (Sep. 1978).

K. Hofmann et. al., Mass Transfer in Ideal and Geometrically Deformed Open Tubes, III. Deformed Metal and Plastic Tubes. *J. Chromatog.* 199, 3, (1980).s

HIGH PERFORMANCE LIQUID CHROMATOGRAPHY METHOD AND APPARATUS

This application is a continuation-in-part of U.S. patent application Ser. No. 08/552,199 filed Nov. 2, 1995, now abandoned.

This invention relates generally to chromatography and more particularly to methods and procedures for effecting improved high performance liquid chromatography (HPLC).

BACKGROUND OF THE INVENTION

The utility of separations by high performance liquid chromatography has been demonstrated over a broad range of applications including the analysis and purification of molecules ranging from low to high molecular weights. In liquid chromatography, as in gas chromatography, there are significant limitations particularly arising out of the time required for analysis. In order to understand fully these limitations, a brief description of the theoretical basis on which these separation processes are based may be useful.

The separation process relies on the fact that a number of component solute molecules in a flowing stream of a fluid percolated through a packed bed of particles, known as the stationary phase, can be efficiently separated from one another. The individual sample components are separated because each component has a different affinity for the stationary phase, leading to a different rate of migration for each component and a different exit time for each component emerging from the column. The separation efficiency is determined by the amount of spreading of the solute band as it traverses the bed or column.

The theoretical background for such separations arose in connection with the so-called "Craig machine" (as described by G. Guiochon et. al. in *Fundamentals of Preparative and Non-Linear Chromatography*, Academic Press (1994) at p. 174) where separations may be considered to be made in a plurality of connected, equal, discrete, hypothetical stages, each volume of which contains both stationary and moving phases and in each of which complete equilibrium is established. Each such stage is called a "theoretical" plate. In such cases the number of theoretical plates in the column is calculated from the degree of separation. The length of the column per calculated theoretical plate is called the "height equivalent to a theoretical plate" or H, and is a measure of the phenomenon of band-broadening. In chromatography, one phase is stationary and the other phase moves past the first phase at a relatively fast rate so that complete equilibrium is, in fact, not attained between the two phases, and of course, no distinct stages are observed. Notwithstanding, plate theory is commonly used to describe the passage of the solute through a chromatographic column to explain band-broadening in terms of a number of rate factors.

In applying plate theory to chromatographic columns, one must assume that all of the solute is present initially in the first plate volume of the column, the distribution coefficient is constant for the solute concentrations encountered, and the solute will rapidly distribute itself between the two phases in each plate volume.

Because columns that provide minimum broadening of separated sample bands are the sine qua non particularly of preparative, modern HPLC systems, the nature of the packing put into the column and manner in which the column is packed, all relative to the solute sought to be recovered, are of great importance. The various processes that determine relative band broadening with consequent deleterious effects on column performance are therefore desirably minimized. It was believed that the effect of each of these processes on the column plate height H can be related by rate theory to such experimental variables as mobile-phase velocity u, packing particle diameter $d_p$, and the solute diffusion coefficient in the mobile phase. The major band broadening processes in HPLC contributing to height equivalent to a theoretical plate, H, are generally considered to be:

(1) eddy diffusion, $a_e d_p$
(2) mobile-phase mass transfer, $a_m d_p^2 u/D$ $\Big\} = Au^n$
(3) longitudinal diffusion, $bD/u = B/u$, and
(4) stagnant mobile-phase mass transfer, $cd_p^2 u = Cu$ where $a_e$, $a_m$, b, and c are plate height coefficients; n is a fractional exponent, A, B, and C are constants for a given column, and D is the diffusion coefficient of the solute in the mobile phase.

Adding these various contributions provides the classical expression describing band-spreading, well-known as the Van Deemter equation, that can be written in simplified form as:

$$H = Au^n + B/u + Cu \qquad \text{(Equ. 1)}$$

A typical H versus u (in cm/sec) plot is shown as in FIG. 1.

In FIG. 1, the A region represents the eddy diffusion term characteristic of the column packing, i.e. flow through the column will find tortuous channels of varying length between the particles. The molecules can then travel different distances while traversing the column, resulting in band-spreading and impairing separation efficiency. Assuming that the flow profile through the column remains constant, the A term supposedly will also remain constant at all values of the linear velocity of fluid flow through the column.

The B region in FIG. 1 is a function of the linear velocity of the fluid through the column and is clearly more significant at low values of that velocity, becoming at high velocities a negligible factor contributing to band-spreading because of the process of axial molecular diffusion of the solute molecules. Such molecular diffusion is driven by concentration gradients, so the relative contribution to band-spreading becomes less as the length of time in the column becomes shorter.

The C region in FIG. 1 varies in opposite sense to B, i.e. its contribution to H increases with increasing flow rate. As the solute molecules flow faster, the separation efficiency becomes limited by the ability of the sample components to diffuse in and out of pores in the particles. The C term therefore represents the mass transfer limitation of this diffusion-driven process. For this reason, the chromatographic process exemplified by FIG. 1 has a finite time analysis boundary. Exemplary of conventional theory, the Van Deemter equation thus teaches that one must settle on a fixed analysis time to achieve maximum separation efficiency.

A family of curves similar to that of FIG. 1 can be obtained by plotting H vs. $\mu$ for variations in column diameter, packing particle size, amount of stationary phase and the like. According to the rate theory as exemplified by the Van Deemter equation, the minima in such family of curves indicates the optimum flow rate of the mobile phase through the column to minimize band-broadening. Importantly, the curve asserts that as the flow rate through the column increases in the C region, the column plate height H and thus the band-broadening also increases.

In describing the function of a HPLC column in a plot such as FIG. 1, it has been customary, as with the Van Deemter curves, for column plate height H to be plotted against linear velocity u of the mobile phase. Since an HPLC process is a diffusion-driven process and since different solute molecules have different diffusion coefficients, one can consider this latter variable in applying the process to a wide range of solutes of different molecular weights. Additionally, the size of the particles in the column may differ from column to column, and may also be considered as another variable, and likewise, the viscosity of the solvent for the solute might be considered. In order to normalize the plots to take these variables into account, one advantageously may employ reduced coordinates, specifically, h in place of H, and $\upsilon$ in place of u, as taught by Giddings and described in *Introduction to Modem Liquid Chromatography*, 2nd Ed., supra, at pp.234–235, to yield a reduced form of the Van Deemter equation as follows:

$$h=a^*+b^*/\upsilon+c^*\upsilon, \quad \text{(Equ. 2)}$$

or $$H=a^*d_p+b^*D/u+c^*ud_p/D \quad \text{(Equ. 3)}$$

wherein the coordinate h is defined as $H/d_p$ where $d_p$ is the particle diameter, and accordingly h is a dimensionless coordinate. Similarly, the dimensionless coordinate $\upsilon$ is defined as $ud_p/D$ where D is the diffusion coefficient of the solute in the mobile phase. It will be recognized that $\upsilon$ is also known as the Péclet number. It should be stressed, however, that the reduced coordinate or Péclet number, $\upsilon$, as used in the instant exposition of the present invention, is descriptive of fluid flow through the channels in the interstitial volume between particles in the column, and should not be considered as descriptive of fluid flow within the pores of porous particles constituting the packed bed in the column.

From Equ. 3, it will be seen that the eddy diffusion term, $a^*d_p$, is a function of particle size. Thus, the Van Deemter reduced equation predicts that as the particle size increases the efficiency should decrease. The longitudinal diffusion term, $b^*D/u$, is shown as a function of both the fluid velocity and the diffusion coefficient, an inverse relationship indicating that for small molecules at very low fluid velocities, this term will be more significant. As the fluid velocity increases, this term will be dominated by the mass transfer term. The latter term, $c^*ud_p/D$, is shown as a function of all three variables, i.e. the particle size, the fluid velocity and the diffusion coefficient. As the fluid velocity increases, the equation predicts that the mass transfer term will dominate the efficiency with a deterioration proportional to the product of the velocity and particle diameter. For a given diffusion coefficient, the efficiency according to the Van Deemter equation should therefore always decrease as a function of the fluid velocity in this region. It will be shown hereinafter that these aspects of the Van Deemter equation are not valid for flow in the turbulent regime.

J. C. Giddings in *Analytical Chemistry*, Vol. 35, 1338, (1963), proposes that the $a^*$ term in Equ. 3 is coupled with mass transfer in the mobile phase to yield a term that is less than $a^*d_p$ or $c^*\upsilon$ alone. Giddings asserts that this coupling theory predicts that plate height approaches a constant value, i.e., at high flow rates the plate height is independent of flow velocity, and asserts that he has evidence of a plate height value as low as 2.5 in liquid chromatography. The same author, subsequently in *Journal of Chromatography*, Vol. 13, 301 (1964), writes that "... the value of h cannot be reduced much below 2, i.e., the plate height H cannot be pushed much below two particle diameters", presenting curves that predict that the optimum plate height is to be found at a reduced velocity between 1 and 2.

It will be appreciated that minimization of band-broadening is desirable to insure that one obtains optimum separation of solutes, particularly in analytical chromatography, and product purity, particularly in preparative chromatography. While these goals are specifically true in the separation of biological macromolecules such as industrial enzymes, various proteins for use in therapeutic and diagnostic procedures and the like, frequently such desired molecules are generated in only minute quantities in a very large volume of fluid and are very large with a correspondingly small diffusion coefficient. Thus, separation of the desired molecules by HPLC would be agonizingly slow and unduly expensive if limited to the mobile phase flow rate dictated as optimal by the Van Deemter curves. Additionally, biologicals may degrade in time while in the preparative solution, either thermally or due to the presence of proteases and the like, so speedy separation is very desirable. The efficiency of production achieved with a liquid chromatographic separation process for biological macromolecules can be described in terms of amount-of-product/dollar. To achieve optimum production, both production speed and capacity are important considerations that are currently not well met.

Efforts have been made to create HPLC systems in which separations are characterized by both high resolution and high time rate of volume processing. For example, the process disclosed and claimed in U.S. Pat. No. 5,019,270 (hereinafter the '270 patent), inter alia involves the flow of a fluid mixture of solutes through a matrix formed with two sets of interconnected pores, each set having a mean diameter that is substantially different than the other set. To effect the process, the rate of convective fluid flow, apparently under a pressure gradient, through the set of pores with the smaller mean diameter must exceed a threshold velocity that exceeds the rate of diffusion of the solute through that set of smaller pores.

Similarly, U.S. Pat. No. 5,228,989 (hereinafter the '989 patent), a continuation of a division of the '270 patent, teaches forming columns by packing particles characterized as having pore structures that are bimodal in that the particles have pores that lie within two different ranges of diameters with a specific ratio of particle diameter to the mean diameter of the pores of the larger range. U.S. Pat. No. 5,384,042 (hereinafter the '042 patent), a division of the '989 patent, discloses and claims a matrix formed essentially of the particles claimed in the '989 patent.

Notwithstanding the assertions that the teachings of the '270, '989 and '042 patents uncouples the phenomenon of band-spreading from velocity of fluid flow through a chromatographic column, it should be noted that the validity of the Van Deemter hypothesis is essentially unchallenged therein inasmuch as these patents state that the C term will not be completely independent of bed velocity and ascribe the claimed improved performance to the existence of the two related sets of pores.

Another example of pertinent prior art is set forth in *Introduction to Liquid Chromatography*, 2nd Ed., Snyder and Kirkland, John Wiley & Sons, N.Y. (1979), presently considered one of the authoritative textbooks on the subject, which displays at p. 238, a table 5.25 characterized as applying to "probably 99% of all LC separations for the foreseeable future.". That table is said to dictate the conclusion that "A higher operating pressure generally yields larger N values (assuming L is increased proportionately)... However, the advantage of a major increase in P (e.g. ten-fold as in Table 5.25) is only important for small values of $d_p$ and/or large values of t. With small particles (5–10 μm) and separation times of 15 min. to 2.5 hr., a 10-fold increase in P yields roughly a 2-fold increase in N. For much smaller particles and long separation times, a 10-fold increase in P can translate into a ten-fold increase in N. However, the experimental conditions involved are totally impractical in that separation times are much too long, and the values of $d_p$ are nonoptimum." (Where N is the number of plates, P is the pressure, $d_p$ is the particle size and L is the column length). The text continues as follows: "As separation time t increases, the optimum value of $d_p$ shifts to higher values, for example, 5 μm for a separation time of 1 day. At higher operating pressures, lower values of $d_p$ are favored . . . so because $D_m$ decreases with increasing sample molecular weight, the optimum value of $d_p$ also decreases." The table on page 241 asserts that the optimum $d_p$ value for a solute having a molecular weight of 300,000 would be from about 0.03 to 0.1 μm, and the text concludes with the statements "From the preceding data we see that submicron particles are decidedly advantageous for the separation of large molecules" and ". . . pressures above 5000 psi do not appear worthwhile for LC separation". (p.240). As will be apparent hereinafter, the present invention is in substantial contradistinction to these assertions and conclusions characteristic of the prior art.

A theory of chromatography expounded by M. Golay (*Gas Chromatography*, D. H. Desty, ed, p. 36, Buttersworths, London, 1958) is based on a number of assumptions that are correct only for laminar flow through a column. This was confirmed by J. C. Giddings (Advances in the Theory of Plate Height in Gas Chromatography, *Analytical Chemistry*, Vol. 35, No. 4, April 1963, pp. 439–448) who, noting shortcomings of the Van Deemter equation, asserted that the equation was incapable of successfully predicting a numerical plate height value in chromatographic columns from independent data because it contains no provision for fixing the magnitude of the effective film thickness, and contains errors and omissions relating to eddy diffusion, gas phase mass transfer and liquid film transfer.

V. Pretorius and T. Smuts (Turbulent Flow Chromatography: a New Approach to Faster Analysis, *Analytical Chemistry*, Vol. 38, No. 2, February 1966, pp. 274–280) remark that all previous studies of minimum time required to resolve a given pair of solutes had been solely concerned with laminar flow of the mobile phase. The Pretorius et al. paper shows that if chromatography is carried out in open tubular columns with turbulent instead of laminar flow, minimum analysis time can be reduced significantly. Pretorius et al. note that under turbulent conditions the Golay expression fails, and refer particularly to the prior studies of band dispersion under turbulent conditions provided by R. Aris in *Proc. Roy. Soc*, A235, 67 (1956); ibid, A252, 538 (1959) to derive equations that are deemed general forms of the Golay expression supposedly valid for both laminar and turbulent flow. Pretorius et al. provide plots showing that plate height, both experimental and calculated according to the new equations, reduces dramatically on transition at a Reynolds number of about $10^3$ from laminar to turbulent flow through open tubes. The paper concludes that by employing turbulent rather than laminar flow, analysis times for gas chromatography are improved by about an order of magnitude. The authors speculate that for chromatography where the mobile phase is liquid, analysis time should be shortened by a factor of about $10^4$, based on their extrapolation of the comparison of analysis times in conventional gas and liquid chromatographies using laminar flow. Pretorius et al. also argue that the length of open tubular columns used in liquid chromatography with turbulent flow must be about ten times as long as for laminar flow, that simple separations would require pressure drops of several atmospheres, and more difficult separations imply pressure drops of more than 100 atmospheres. The use of turbulent flow liquid chromatography to obtain preparative separations with high accuracy and high speed would appear to be contraindicated by the teachings of Pretorius et al., who notes at page 280, col. 2, that a separation in a tube with a diameter of 0.1 cm. and a length of 2000 cm. (with a separation factor of 1.5) would apparently take 24 days, and surmises that with a separation factor of 0.75, the analysis time might be shortened to about 6 days.

The utility of turbulent flow in capillary chromatographic columns was advocated many years ago as an attractive means for achieving highly efficient separations, but was not extended to packed columns since the pressure drop necessary to obtain turbulent flow was considered too large for practical considerations. Cf. M. Martin et. al., Influence of Retention on Band Broadening in Turbulent Flow Liquid and Gas Chromatography., *Anal. Chem.*, 54, 1533–1540 (1982). A similar conclusion was reached by I. Halasz in Mass Transfer in Ideal and Geometrically Deformed Open Tubes - II. Potential Applications of Ideal and Coiled Tubes in Liquid Chromatography, *J. Chromatogr*, 173, 229–247, (1979) which specifically declines to discuss liquid chromatography in the turbulent region because the specific permeability is at least 3 less than in laminar flow, the h values are ten times higher than theory predicts, high pressure drops are unacceptable, and injection is very difficult at high inlet pressures. Further, it was recognized that maintenance of the stationary phase in a chromatographic milieu under turbulent flow conditions was difficult at best and appeared impractical because of the high shear forces involved.

D. S. Horne et. al., A Comparison of Mobile-Phase Dispersion in Gas and Liquid Chromatography, *Sep. Science*, 1(5), 531–554 (1966), presented a study of the fluid dynamics of flow through columns and recognized that at very high liquid velocities, turbulence influences the rate of dispersion in the flow. The highest velocity that is shown in the liquid experiments was log v=3.8 which is approximately around a reduced velocity of 6,500. The paper states that at very high velocities and Reynolds numbers in excess of about 10, the reduced plate height becomes independent of the velocity. The paper was based on studies conducted with columns prepared with non-porous glass beads of 500 μm diameter packed with column-to-particle diameter ratios of 10 to 30. No chromatographic separations were effected inasmuch as no solute was retained on the beads. Similarly, H. Kaizuma et. al., Evaluation of Coupling and Turbulence by the Dynamical Comparison of Gas and Liquid Chromatography, *J. Chrom. Science*, Vol. 8, 630–534 (November 1970), in another study of the fluid dynamics of flow through columns packed with 500 μm non-porous, spherical glass beads that were not chromatographically active, notes that coupling and turbulence will cause plate height vs. velocity plots to differ radically from the Van Deemter form, based on the use of input column pressures up to 123 atm. to get high velocity extremes. This latter paper shows that a log reduced plate height vs. log reduced velocity plot for liquids extends to reduced velocities in excess of 8,000 and shows a maximum somewhere around about 5000 before the plate heights (around 10) begin to drop. The paper concludes that turbulence does not appear to be important in LC.

With respect to the flow of an incompressible viscous fluid through a hollow cylindrical pipe or tube of uniform cross-section and relatively smooth walls, it has long been recognized that there is a critical or transition flow velocity separating steady laminar flow (i.e. where the pressure drop is proportional to the velocity) and the fluid moves in layers without irregular large fluctuations, from a regime of irregular and unsteady, or turbulent, flow (i.e. where the pressure drop varies more nearly with the square of the velocity and the local velocities and pressures in the fluid fluctuate irregularly). Such flows can be described in terms of the Reynolds number Re defined as $$Re = \rho \upsilon d/\mu \qquad \text{(Equ. 4)}$$

where $\rho$ is the fluid density (g/cm$^3$), $\upsilon$ is the fluid velocity (cm/sec), d is the pipe diameter (cm) and $\mu$ is the fluid viscosity (g/cmsec). The Reynolds number, having no dimensional units, thus serves as a criterion of the type of fluid flow. For example, it is well known that ordinarily, if the Reynolds number is small, e.g. less than about 2100, the flow in such smooth-walled tubes is laminar, and at higher Reynolds numbers, e.g. above about 3000, the flow will be turbulent. Flow at Reynolds numbers between about 2100 and 3000 constitutes the critical transition stage. The values of the Reynolds number, as noted above, depend to some extent on the smoothness of the interior surface of the conduit through which the fluid flows. Where the interior surface of the conduit is rough, i.e. irregular, the transition to turbulent flow will occur at somewhat lower Reynolds numbers. Because turbulent flow, at least in aqueous-type fluids, was largely believed to occur only if the Reynolds number exceeded about 2100, the impracticality of obtaining such flow through the packed bed of a chromatographic column seemed clear inasmuch as one cannot approach this Reynolds number except at pressures that would require massive pressure vessels and, more importantly, collapse porous particles in the column.

OBJECTS OF THE INVENTION

A principal object of the present invention is to provide improved chromatographic apparatus and processes for high capacity, high resolution separation of solutes. Yet another important object of the present invention is to provide such apparatus and processes which, contrary to the teachings of the prior art, when used in HPLC for separation of solutes, will exhibit a characteristic curve that is substantially the inverse of the Van Deemter curve in that band-broadening increases as the mobile phase velocity through the HPLC column increases from the B segment to the A segment and diminishes as the mobile phase velocity through the column increases beyond the A segment. Other objects of the present invention are to provide such apparatus and processes as will dramatically enhance both the speed and capacity of both analytical and preparative chromatography for both small and large molecules such as biologicals and the like, to provide such apparatus and processes operative with mobile phase velocities considerably greater than any heretofore employed with significantly improved results, to provide such apparatus and processes that are operative with packed particle beds in which the particles are substantially larger that those commonly used by the prior art, and to provide such apparatus and processes that are operative at pressures considerably below those taught by the prior art for turbulent flow liquid chromatography.

SUMMARY OF THE INVENTION

To these ends the present invention is directed to novel methods of performing liquid chromatography wherein a chromatography column or body is formed as a substantially uniformly distributed multiplicity of rigid, solid, porous particles having substantially uniform mean cross-section dimensions or diameters of not less than about 30 $\mu$m, typically 50 $\mu$m or greater up to, but not limited to, 1000 $\mu$m in certain instances as will be delineated hereinafter. The term "particle" as used herein should not be construed as limited to any particular form or shape, regardless of symmetry or lack thereof, aspect ratio, regularity and the like. The term "solid" as used herein, is intended to refer to the physical state of the matter and should not be construed to exclude porous particles. The particles are selected from a range of various sizes and shapes and are held together in a body or column as by pressure, sintering and the like so that interstitial channels having a total interstitial volume of not less than about 45% of the total volume of the column are formed between the particles. The surfaces of the particles, including the inner surfaces of the pores in the particles, are chromatographically active, as by being coated with chromatographic stationary phase layers. The method includes the step of flowing through the column a fluid mixture containing at least one solute or suspended phase that is interactive with the particles' surfaces in order to load the column. Because of the nature of the particles and packing in the column, the flow of the fluid mixture through the column can be at a high flow rate, preferably at an average reduced velocity (as hereinafter defined) greater than about 5000, and including, in certain instances to be described hereinafter, reduced velocities values as high as 70,000 or higher. It is believed that under such conditions, turbulent flow of the mixture is induced within at least a major portion of the interstitial volume, and it is postulated that such turbulent flow in fact enhances the rate of mass transfer, thus increasing the dynamic capacity of the column. The present invention further establishes that unexpectedly the combination of chromatographically active particles with very large average diameters, (e.g. $d_p$ of 500 $\mu$m or more) with turbulent flow, particularly at high values of reduced flow velocity, $\upsilon$, (e.g. 40,000 or more) provide reduced plate height values of 1 or less.

The methods of the present invention may also include the step, after flowing the mixture with its solute through the column, of passing eluant fluid through the column at a reduced velocity also preferably greater than about 5000. As will be shown, by flowing eluant fluid through the interstitial volume of the column at such reduced velocities, band-spreading experienced by solute eluted from the column will, quite contrary to the Van Deemter prediction, the band spreading under these conditions is an inverse function of the Reynolds number for the eluant flow and is a direct function of the magnitude of the diffusion coefficient of said solute in said eluant fluid, the molecular weight of the solute being a large factor in the diffusion coefficient.

The invention also is embodied in chromatography apparatus comprising a chromatographic column formed as a packed multiplicity of rigid solid particles having substantially uniform mean diameters of not less than about 30 $\mu$m. These particles are shaped and selected in a range of sizes and shapes and packed at a pressure sufficient to form between the particles interstitial channels or spaces defining an interstitial volume between said particles of not less than about 45% of the total volume of said column. The surfaces of those particles are chromatographically active, as by having been coated with one or more chromatographically stationary phase layers. In a preferred embodiment, particularly where the particles of the column are near the lower end of the acceptable range of cross-section dimensions, the particles are irregular as hereinafter defined.

Means are provided for flowing through the column a fluid mixture at a reduced velocity of at least about 5000, such reduced velocity being believed to be sufficient to induce turbulent flow of the mixture within at least a major portion of the interstitial volume, the mixture containing at least one solute that is interactive with the stationary phase layers. The invention further includes means for flowing eluant fluid through a charged column at a velocity selected such that band spreading of solute eluted by the eluant fluid from the column is an inverse function of both the Reynolds number for the eluant flow and of the magnitude of the molecular weight of the solute in the eluant fluid. To this end, the flow of eluant fluid is effected at a reduced velocity greater than about 5000.

In yet another embodiment of the present invention, particularly useful for separating solute molecules of relatively small molecular weight (e.g. even as low as 50 or less), a packed bed of particles with average diameters of several hundred (e.g. 500 $\mu$m or more) is provided. This embodiment also includes means for flowing through that column a fluid mixture of sample and eluant at a reduced velocity as high as 70,000 or higher, such reduced velocity being believed to provide the requisite turbulent flow. At such typical values of $d_p$ and $\upsilon$ for such column, it has now unexpectedly been found that the reduced plate height h is inversely related to the velocity of the mobile phase, and is not independent thereof as believed in the prior art.

It has also been found that in chromatographic processes in which solutes introduced into a packed bed of chromatographically active particulates tend to become non-specifically bound, such non-specific binding is reduced simply by flowing the solute in a liquid mixture through the column at an average reduced velocity greater than about 5,000, followed immediately with an eluant flow at least at the same average reduced velocity.

The foregoing and other objects of the present invention will in part be obvious and will in part appear hereinafter. The invention accordingly comprises the apparatus possessing the construction and arrangement of parts exemplified in the following detailed disclosure, and the method comprising the several steps and the relation and order of one or more of such steps with respect to the others, the scope of the application of which will be indicated in the claims.

For a fuller understanding of the nature and objects of the present invention, reference should be had to the following detailed description taken in connection with the drawings wherein line numerals denote like parts.

DETAILED DESCRIPTION

The present invention takes advantage of a number of discoveries that the conventional wisdom regarding liquid chromatography is neither thorough nor completely accurate. For example, as noted above, the Van Deemter equation is limited to situations where the mobile phase flow is essentially laminar and the present invention is believed to establish the invalidity of the Van Deemter equation where the mobile phase flow is turbulent.

Figure 1:
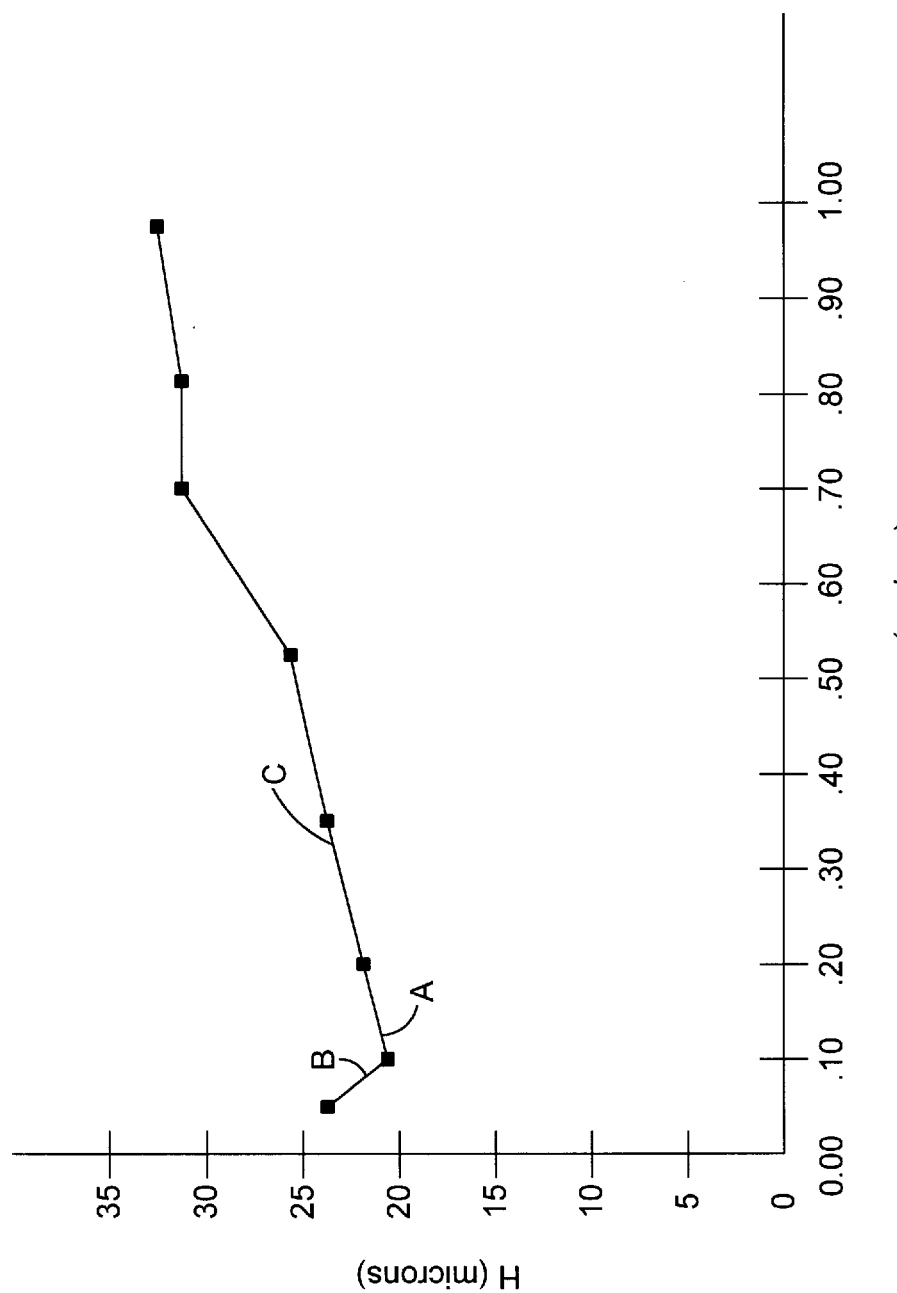
FIG. 1 is an exemplary prior art Van Deemter curve where a typical column plate height H is plotted against u (in cm/sec)
Figure 2:
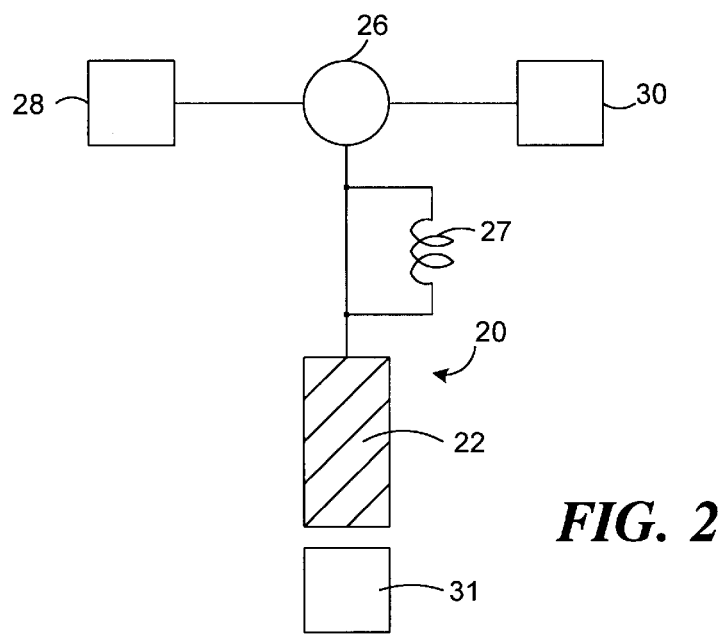
FIG. 2 is a schematic diagram of apparatus embodying the principles of the present invention.

One aspect of the present invention, as shown in FIG. 2 schematically, is embodied in chromatography apparatus comprising a chromatographic column 20 formed as a packed multiplicity of rigid, solid particles 22 that, in a first embodiment of the present invention, have substantially uniform mean diameters of not less than about 30 $\mu$m. The term "mean diameter" as used herein is intended to mean the average (mean) diameter or cross-section dimension of the particles regardless of particle configuration and is not to be construed as limited to particles that are necessarily spherical or regular solids, the value of such mean diameter typically being within a distribution of diameters at a confidence coefficient of about 95%. Indeed, a preferred aspect of the present invention is the irregularity of particles' shape, as will be delineated hereinafter. The term "irregular" as used herein is intended not only to be defined as lacking conformity of form, inasmuch as the particles can be present in a mixed multiplicity of various polyhedral configurations, but is intended to include short fibers as well as solids of revolution such as generally spherical, conoidal, ellipsoidal and the like type of particles with rough, uneven or scabrous surfaces.

Figure 3:
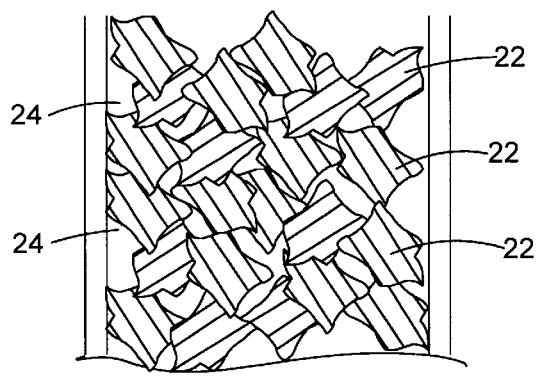
FIG. 3 is an idealized, enlarged view of a portion through one embodiment of the column of FIG. 2.

The particles of the present invention are preferably formed from materials that are incompressible, which term is to be understood to mean that the time rate of changes of the densities and volumes of the particles under pressures of at least about $5 \times 10^3$ psi, (including outlet column frit retainer) remains substantially zero, and the particles therefore will substantially resist plastic deformation even at such high pressure. The particles of the present invention are shaped and selected in a range of sizes and shapes such that they can be packed at a pressure sufficient to form a column characterized in having interstitial channels 24, as shown particularly in FIG. 3, formed between particles 22. Because of the irregularity of the particles, it will be recognized that the interior walls of such channels are necessarily quite rough in configuration. While it is believed that at least the majority of channels 24 have mean cross-section diameters substantially not less than about 4 $\mu$m, the interstitial volume fraction (i.e. the total volume of interstitial channels 24 between the particles) should not be less than about 45% of the total volume of column 20. It will be appreciated that typical columns of the prior art have interstitial volume fractions less than about 45%, more particularly ranging from about 35% to 42%. The surfaces of particles 22 are chromatographically active either per se as is well known in the art, or by treatment, as by coating, with any of the many known chromatographically active, stationary phase layers, also as well known in the art.

Particles 22 may be pellicular, or to increase active surface area, are preferably porous with the intraparticle pores typically having mean diameters lying, for example, within a range of about 60 Å to 5,000 Å. As a result of the particle irregularity, coupled with an interstitial volume fraction of not less than about 45%, it is believed that turbulent flow through the interstitial channels of the column of the present invention can surprisingly be induced at Reynolds numbers well below 10.

The interstitial volume, $V_i$, for a column formed of porous particles, can be defined as:

$$V_i = V - V_p - V_s \qquad \text{(Equ. 5)}$$

where V is the total volume of the empty column;
$V_p$ is the total volume of pores in the particles themselves; and
$V_s$ is the total volume of the skeletons or frameworks of the particles.

The interstitial volume, $V_i$, for a column formed of non-porous particles, can be defined as:

$$V_i = V - V_x \qquad \text{(Equ. 6)}$$

where $V_x$ is the total volume of the particles.

Hg intrusion analysis, a well-known technique, can be used to determine the interstitial volume in columns of imporous as well as columns of porous particles.

In the present invention, means, such as pump 26 coupled to the proximal end of column 20, is provided for flowing through at least a major portion of the interstitial volume, a fluid mixture (from an appropriate source such as reservoir 28) and/or a solute (from an appropriate loop injector such as 27), at a reduced velocity (i.e., $ud_p/D$ as above-defined) that, in this first embodiment of the present invention, is substantially above about 5000. It will be seen that the latter is an approximate value at which the slope of the h/υ curve begins to decrease along the reduced coordinate h (i.e. $H/d_p$) axis, indicating an improvement in efficiency with increasing reduced velocity. It is believed that turbulent flow of the mixture is induced in the column of the first embodiment of present invention at a flow velocity corresponding to a reduced velocity value of about 5000. The present invention further includes means, such as pump 26 for flowing eluant fluid (typically from another appropriate reservoir or storage tank 30) through a charged column (i.e. column 20 in which at least some of the chromatographically active surfaces have solute molecules bound thereto as a result of flowing the solute mixture through the column initially). The solute molecules eluted by the eluant fluid are detected, typically optically by detector 31, of a type and in a manner well known in the prior art, disposed at the distal end of column 20. The eluant flow through column 20 must be at a linear velocity corresponding to a reduced velocity which, for the first embodiment of the present invention, is above about 5000, so that band spreading of solute eluted by the eluant fluid from the column is an inverse function of the Reynolds number for the eluant flow and is a direct function of the magnitude of the diffusion coefficient of the solute in the eluant fluid. It will be recognized, that in view of the relationship between the molecular weight of the solute and its diffusion coefficient, the band spreading of solute eluted by the eluant fluid from the column in the present invention can also be defined as an inverse function of the molecular weight of the solute.

Column 20 is typically a hollow, tubular container, formed of a rigid, strong material such as stainless steel or the like, that is chemically inert or unreactive to the fluids to be passed through it. The column may have a small inside diameter, e.g. a few mm., or may be of very large internal diameter, depending on the volume of liquid that is to be chromatographically treated. According to D. S. Horne et. al., A Comparison of Mobile-Phase Dispersion in Gas and Liquid Chromatography, *Sep. Science*, 1(5), 531–554 (1966), the dispersion of bands in beds packed with spherical particles is least desirable, at least at medium flow rates for the mobile phase, at ratios of column diameter-to-particle diameter between about 10 and 30. The present invention is concerned however with very high flow rates to achieve turbulent flow, so column-to-particle diameter ratios do not appear to be critical.

In a preferred embodiment of the present invention, the column is formed by packing particles having a mean diameter not less than about 30 μm, preferably under pressure of at least about $5 \times 10^3$ psi to insure that the column formed will include substantially no voids except for interstitial channels 24 formed between particles 22 in contact with one another, i.e. column 20 has a substantially uniform bulk density. Columns 20 formed in this manner, regardless of whether or not the particles are porous or non-porous, should exhibit interstitial fractions of about 45% or higher. Lower interstitial fractions, typically around 35% for porous, non-rigid polystyrene particles, will not exhibit the requisite reduced fluid velocity except at unacceptably high pressure that will tend to collapse or rupture the particles.

As noted, in order to insure the formation of the desired uniform density column with the preferred interstitial fraction and preclude collapse under operating pressure, the particles used to pack a column in the present invention are rigid solids that must necessarily be incompressible at packing pressure of at least about $5 \times 10^3$ psi, preferably up to pressures as high as about $1 \times 10^4$ psi. To that end, the preferred particles are formed from materials such as alumina, titania, silica, zirconia, vanadia, carbon, various relatively inert metals, and combinations thereof.

The method of the present invention therefore requires that the flow through at least a majority of the interstitial channels in the chromatographic column must be turbulent. It is postulated that the turbulent flow profile is almost flat, as distinguished from the typical parabolic flow profile characteristic of laminar flow through a chromatographic column. More importantly, it is believed that when turbulent flow is induced, a radial component of velocity is superimposed upon the normal diffusion process, altering the normal diffusional process and the band-spreading kinetics in a favorable manner with respect to the efficiency of the column. It is further postulated that in order to induce and sustain turbulent flow though the column, there is a critical relationship between the diameter of the flowing channel and the linear flow velocity whereby the product of these two parameters remains constant with changes in the linear velocity. The need for particles that are rigid and can withstand changes in pressure without plastic deformation, as above-indicated, is therefore very important.

It should be noted that from a practical point of view, if one seeks to employ the ordinary criteria measuring for turbulent flow in a chromatographic column, i.e. to provide a flow at a Reynolds number greater than 2000, such a flow generally cannot be obtained through a densely packed bed. The key to inducing turbulent flow in the column in the method of the present invention lies in the combination of the roughness of the particles together with the high interstitial volume fraction, i.e. >45%. As a result of these factors, it is believed that turbulent flow in chromatographic columns of the present invention has been induced at Reynolds numbers well below even 10.

In carrying out the methods of the present invention with the apparatus of the first-described embodiment of FIG. 2, a number of different batches of particles were employed to form packed columns. The batches differed primarily in that pore diameters were manipulated, i.e. altered selectively from the pore diameters of the uncoated particles, by coating batches of the latter particles with layers of chromatographically active materials. Pore density distributions for each such batch of porous particles were determined in a known manner with polystyrene standard solutions formed of several known different molecular weight polystyrenes, each dissolved in methylene chloride. Specifically, polystyrenes having molecular weights ranging from $2 \times 10^3$ to $6 \times 10^6$ were employed to determine the exclusion limit and the intrusion profile of the particles. Each such polystyrene-standard containing solution was injected into a corresponding bed of porous particles of predetermined size and/or coating. The pore volume was measured by injecting acetone into each such bed as a total permeating probe, and subsequently a solution of $6 \times 10^6$ molecular weight polystyrene as a totally excluded probe. The transit or elution time through the bed for each standard was measured by ultra-violet detection at 254 nM. Percent intrusion was calculated as the elution volume of each probe less the elution volume of the excluded probe, divided by the pore volume.

To measure porosity, a number of batches of particles were examined, the first being a batch (designated herein as CT-50Al-002) of uncoated, unfunctionalized highly irregularly shaped, porous alumina particles having a nominal diameter of 50μ, but an actual mean diameter, as determined by Coulter analysis, of 42.39μ within a 95% confidence factor. Four other batches of particles of nominal 50μ diameters, irrregularly-shaped, porous alumina, but with different degrees of functionalizing immobilized polymer coatings for each batch (respectively designated herein as PS-11-035, PS-9-087, PS-4-090 and PS-10-024) were also examined by the same technique. The four batches with functionalized coatings represent a range of surface coverage of 2.7 to 6.04 percentage weight loss by thermogravimetric analysis. This weight loss occurs due to the combustion of the functionalized polymer coating at elevated temperature during the analysis.

Figure 4:
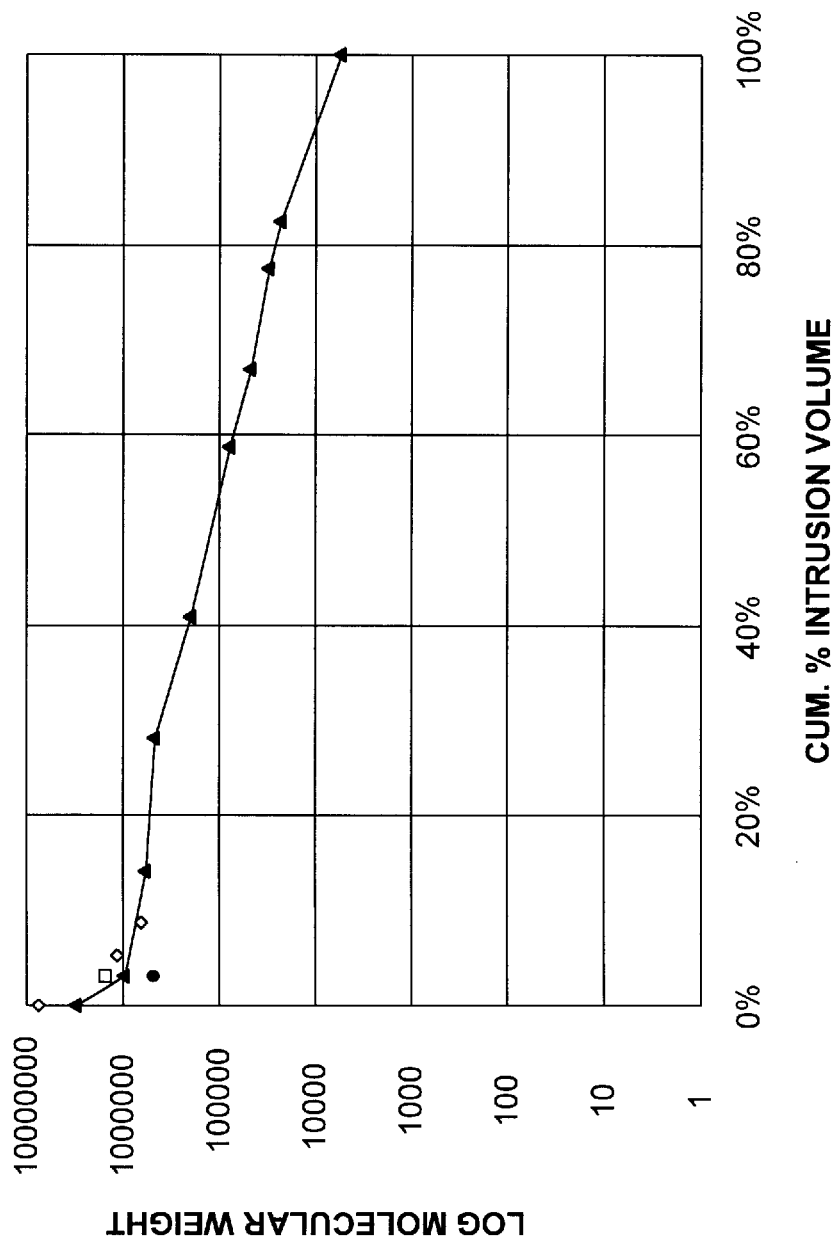
FIG. 4 is a graph of pore size distribution for selected batches of porous particles with different coatings, in which intrusion volume of the particle pores is plotted against the logarithm of the molecular weight of selected solutes.

It will be understood that, inasmuch as the particles described are preferably irregular and are not generally spherical, the term "diameter" as used herein is intended to indicate the average cross-section dimension of the particle. All of these batches of particles were subjected to a series of polystyrene probes of different molecular weights, as above-delineated. The resulting data, plotted as log molecular weight against cumulative percent intrusion, is shown in FIG. 4. It will be apparent that the curves in FIG. 4 are all approximately log-linear with approximately the same slope, so that the lightly coated particles exhibit minor narrowing of the pore diameters. The heavily coated particles however indicate that substantial and linear reduction of the internal pores of the particles had occurred. The diffusion coefficients $D_m$ of the polystyrene standards were calculated according to the formula set forth by G. Guiochon et. al. in *Fundamentals of Preparative and Non-Linear Chromatography, supra*, at p.142.

Individual HPLC columns were prepared using respective batches of irregular, porous, alumina particles of nominal average diameters of 50μ (CT-50Al-002), 20μ (CT-20Al-002), and 10μ (CT-07Al-002), using the following packing protocol. About 2 grams of each batch were slurried in respective multisolvent mixtures, each slurry being transferred to a mechanical device that packed the slurry into respective hollow tubes of 0.46×10 cm. each, under a packing pressure of $5 \times 10^3$ psi. Such columns then exhibited a column-to-particle diameter ratio of at least about 90. The resulting packed columns were removed from the packing apparatus, capped and equilibrated in an appropriate testing solvent. The HPLC system used to evaluate these packed bed columns used in connection with the following Examples employed a commercially available Model 1050 HPLC system from Hewlett Packard Co., Palo Alto, Calif., which system comprised a pump for delivering fluid into the column and an ultra-violet detector of varying wavelength capability for examining the bands eluted from the column. The system for processing data received from the detector was a Model 486/33SX computer available commercially from Acer America, San Jose, Calif. running a software program identified as "HPLC Chemstation", Rev. A.02.00, obtained commercially from Hewlett Packard Co., Palo Alto, Calif.

The following are examples of the preparation, testing and use of liquid chromatography columns embodying the principles of the present invention:

EXAMPLE 1

An HPLC column prepared as described above and packed with batch CT--50Al-002 particles with nominal average diameters of $50\mu$ was evaluated by equilibration in methylene chloride solvent. Standard solutions of various molecular weight polystyrenes, dissolved in methylene chloride, were injected individually into the column. Evaluations were effected at flow rates ranging from 0.2 mL/min up to 20 mL/min. The efficiency of each injection was calculated by measuring the peak width at the half-height point of the detected peak. Elution times for each injection were recorded by measurement with ultra-violet detection at 254 nM. The pressure drop at each flow rate was measured and tabulated. The resulting efficiency data are summarized in graph form in FIG. 5, being plotted in terms of reduced parameter coordinates, h and $v$.

EXAMPLE 2

An HPLC column prepared as described above and packed with batch CT-20Al-002, uncoated, unfunctionalized highly irregularly shaped, porous alumina particles with nominal average diameters of $20\mu$ was evaluated as in Example 1, polystyrene standards of various molecular weights, dissolved in methylene chloride, being injected individually into the column. Evaluations were effected at flow rates, the efficiency of each injection was calculated, elution times were recorded and the pressure drop tabulated, all in accordance with the procedure set forth in Example 1, the resulting efficiency data being set forth in FIG. 6 in coordinates similar to those displayed in FIG. 5.

EXAMPLE 3

An HPLC column prepared as described above and packed with batch CT-07Al-002, uncoated, unfunctionalized highly irregularly shaped, porous alumina particles with nominal average diameters of $10\mu$ was evaluated as in Example 1, polystyrene standards of various molecular weights, dissolved in methylene chloride, being injected individually into the column. Evaluations were effected at flow rates, the efficiency of each injection was calculated, elution times were recorded and the pressure drop tabulated, all as set forth in Example 1, the resulting efficiency data being set forth in FIG. 7 in the same coordinates as displayed in FIGS. 5 and 6.

EXAMPLE 4

Figure 8:
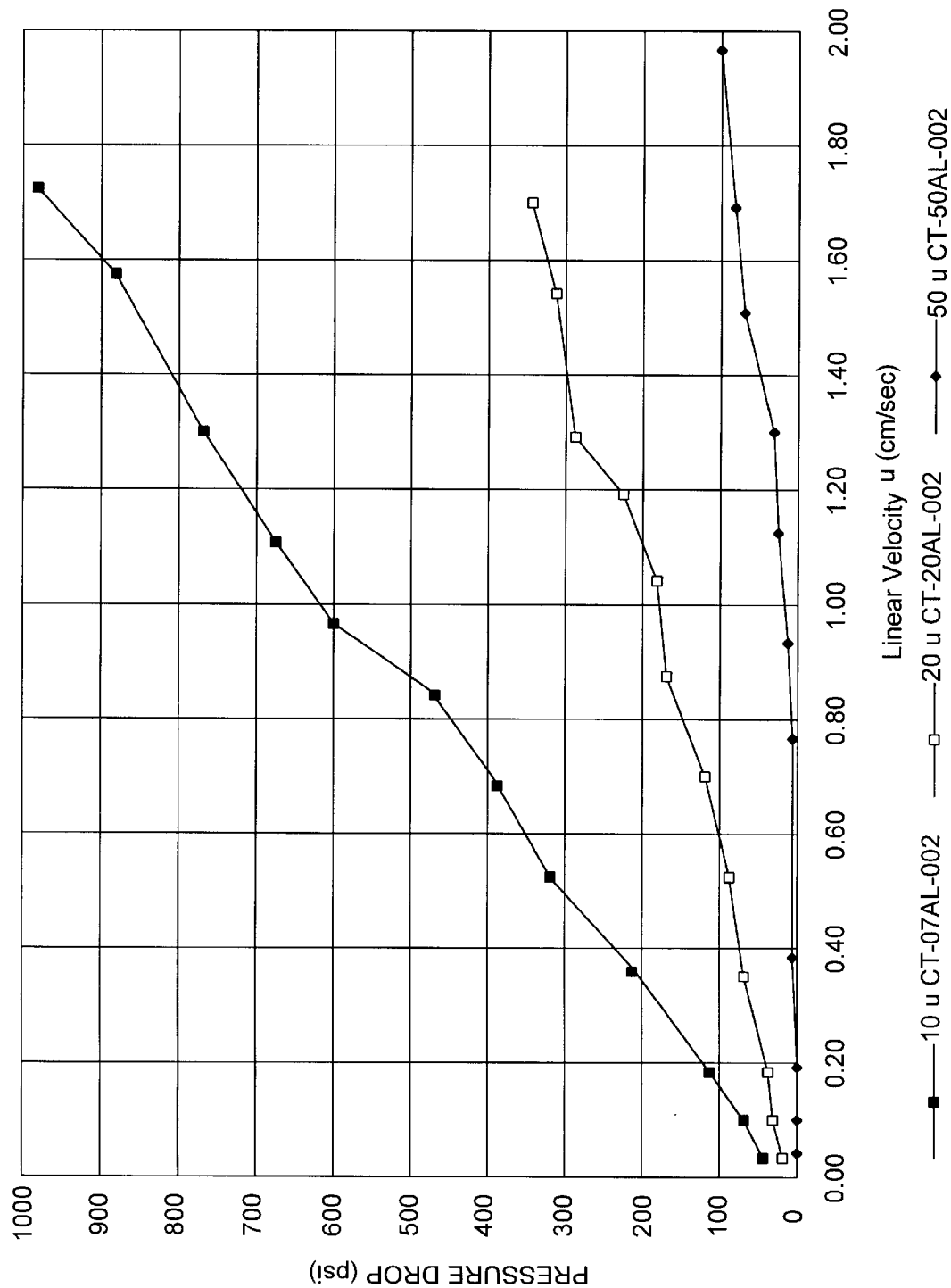
FIG. 8 is a plot of the data obtained from Examples 1, 2 and 3, with regard to the back-pressure drop in psi measured against the fluid linear velocity, supplementing the graphs of FIGS. 5, 6, and 7.

The back pressure for each of the columns eluted in Examples 1, 2 and 3 was measured and recorded. The data obtained are plotted as pressure drop in psi vs linear velocity in cm/sec in FIG. 8.

EXAMPLE 5

Figure 9:
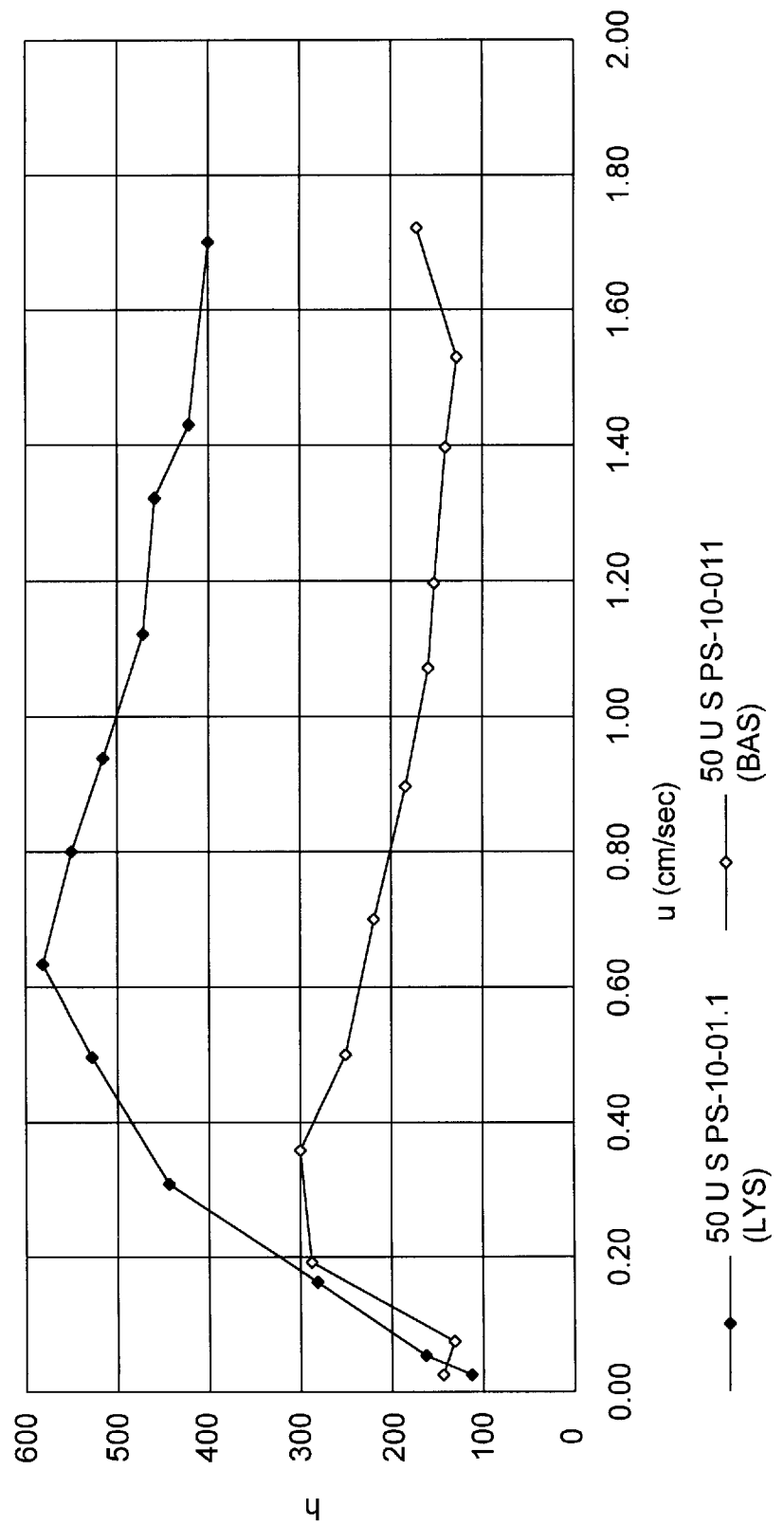
FIG. 9 is a graph of the analysis of two test solutes, each of a different high molecular weight protein, eluted at flow rates from 0.5 ml/min to 10 ml/min from an HPLC column of the present invention packed with particles with nominal average dimensions of 50$\mu$, derivatized to provide a cation exchange capability, the resulting data are plotted in terms of reduced plate height h vs. $\mu$ in cm/sec.

HPLC columns prepared as described above and packed with batch PS-10-011 particles with nominal average dimensions of $50\mu$, was derivatized with a surface chemistry containing a functionality so as to be suitable for separation by cation exchange. The column was equilibrated with a 20 mM neutral pH tris (trishydroxymethylaminomethane) buffer containing 2M NaCl. Samples of 60 mg/ml of BSA (bovine serum albumin) and lysozyme, both obtained from Sigma Chemical Co., St. Louis, Mo., molecular weights of about 67,000 and 13,000 respectively were dissolved in the mobile phase, injected into the column and eluted at flow rates ranging from 0.5 mL/min to 10 mL/min. The resulting data are plotted in FIG. 9 in terms of h and u.

EXAMPLE 6

Figure 10:
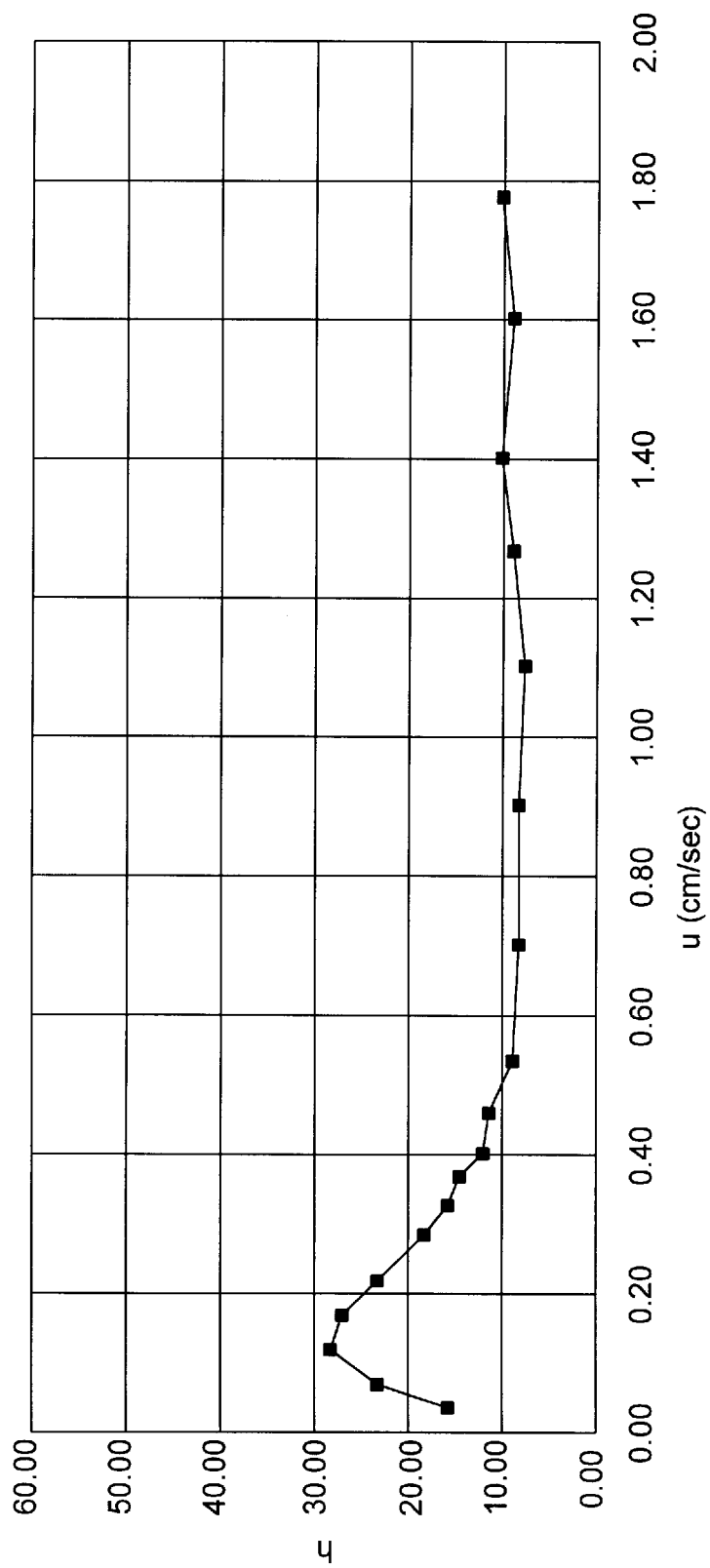
FIG. 10 is a graph of the analysis of one of the same test solutes, eluted at the same flow rates from a column of the same size particles, and plotted in the same coordinates on the same scale, all as in connection with FIG. 9, in which however the particles are derivatized instead to provide an anion exchange capability.

An HPLC column prepared as described above and packed with batch PS-14-037 particles with nominal average dimensions of $50\mu$, were derivatized with a surface chemistry containing a quaternized amine functionality so as to confer a separation capability by anion exchange. The column was equilibrated as set forth in Example 5, and a sample of 60 mg/mL of the same BSA as in Example 5 was dissolved in the mobile phase, injected into the column and eluted at flow rates according to the procedure set forth in Example 5. The resulting data are plotted in FIG. 10 in the same coordinates and scale as employed in FIG. 9.

EXAMPLE 7

Figure 11:
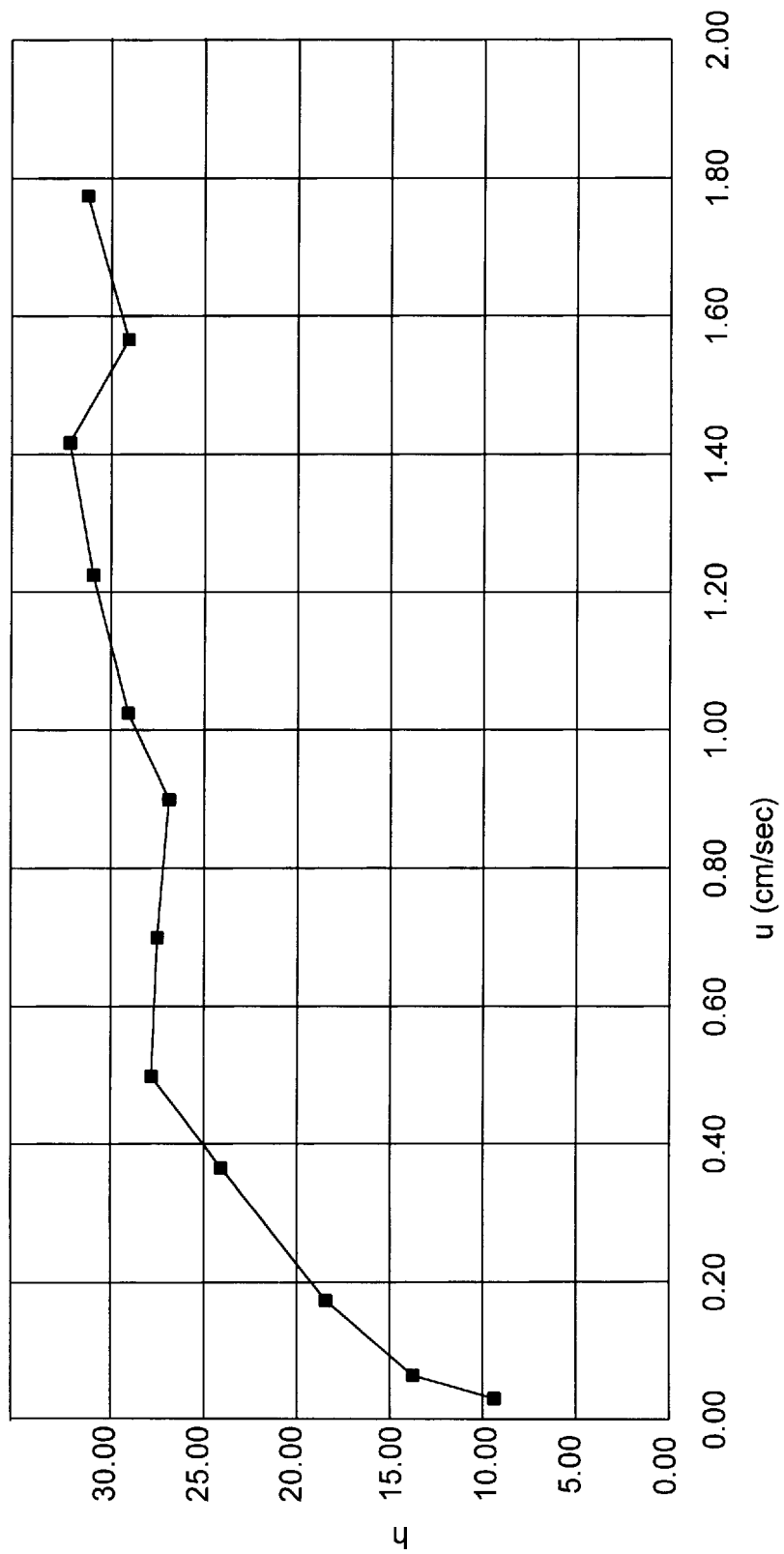
FIG. 11 is a graph of the analysis of one of the same test solutes used in connection with FIG. 9 eluted in the same manner from a chromatographic column of the present invention packed with particles of nominally 20$\mu$ derivatized to provide an anion exchange capability, plotted in the same coordinates as in FIG. 9.

A column prepared as described above and packed with batch PS-11-090 (nominally $20\mu$ particles) was derivatized with a surface chemistry containing a quaternized amine functionality so as provide separation capability by anion exchange. The column was equilibrated and tested as in Example 5, and the resulting data are plotted in FIG. 11.

EXAMPLE 8

Figure 12:
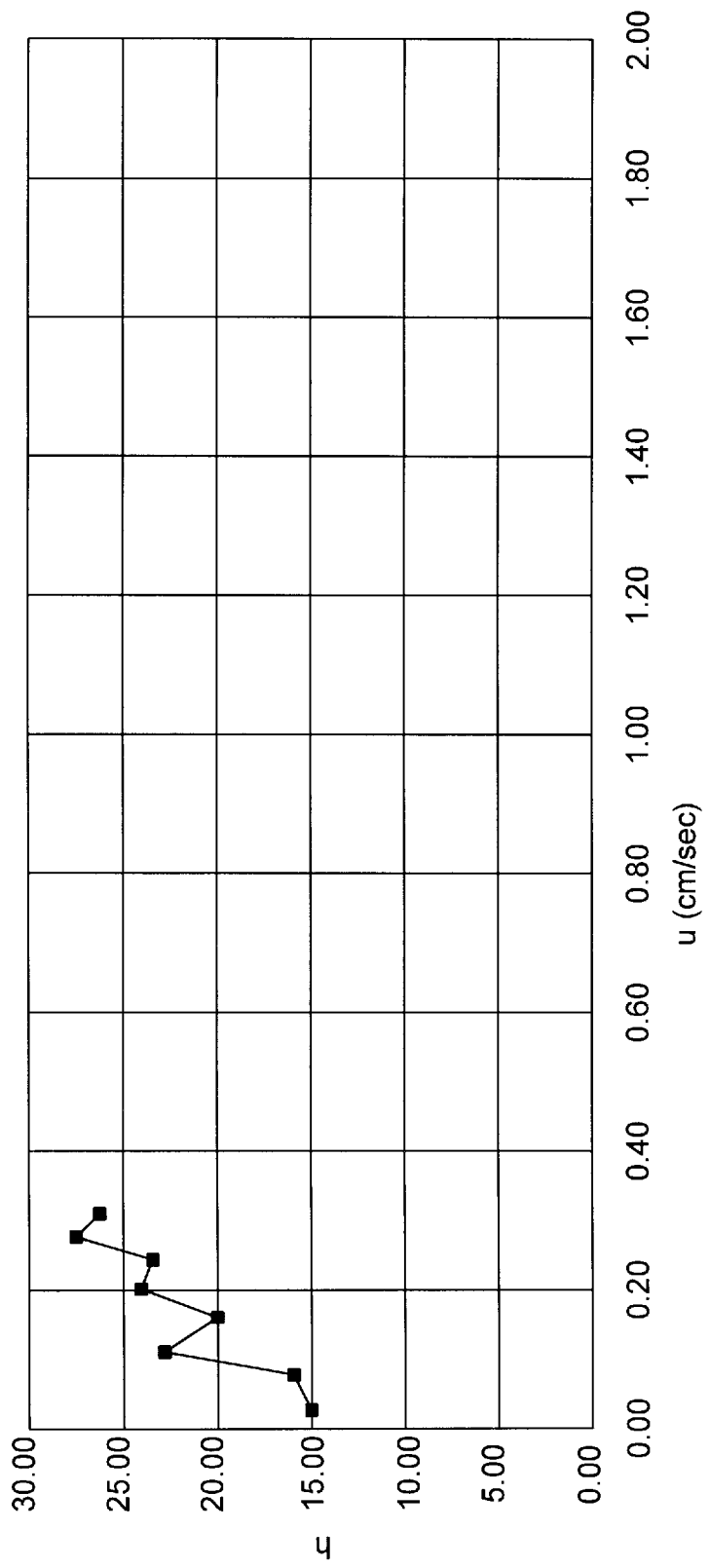
FIG. 12 is a graph of the analysis of the same test solutes used in connection with FIG. 11 eluted in the same manner from a chromatographic column of the present invention packed with particles of nominally 10$\mu$ derivatized to provide an anion exchange capability, plotted in the same coordinates and scale as in FIG. 11.

A column prepared as described above and packed with batch PS-11-027 (nominally $10\mu$ particles), was derivatized with a surface chemistry containing a quaternized amine functionality so as provide separation capability by anion exchange. The column was equilibrated and tested as in Example 5, and the resulting data are plotted in FIG. 12.

EXAMPLE 9

To illustrate the high speed and resolution of the method of the present invention as applied particularly to preparative chromatography, an HPLC column prepared as described above and packed with batch CT-50Al-002 particles with nominal average dimensions of $50\mu$, was derivatized with a surface chemistry containing a quaternized amine functionality and evaluated under gradient elution with a Prosys HPLC instrument manufactured by BioSepra, Marlborough, Mass. This instrument included four pumps with a maximum flow rate of 30 mL/min for each pump so that the total maximum flow rate was 120 mL/min. The instrument also comprised a static mixer, an ultraviolet detector measuring at 280 nm, a 5 mL syringe loader and injection loop, an internal software program for processing the detector output and other data, and a screen for displaying output data. In conjunction with this Prosys instrument, a tertiary HPLC pump (Model No. 6200A from Hitachi Instruments, Tokyo, Japan) having a maximum flow rate of 30 mL/min was provided, the two pumping systems being configured together with a T-junction before the mixer in the Prosys instrument, thereby providing a maximum flow rate of 150 mL/min.

Figure 13:
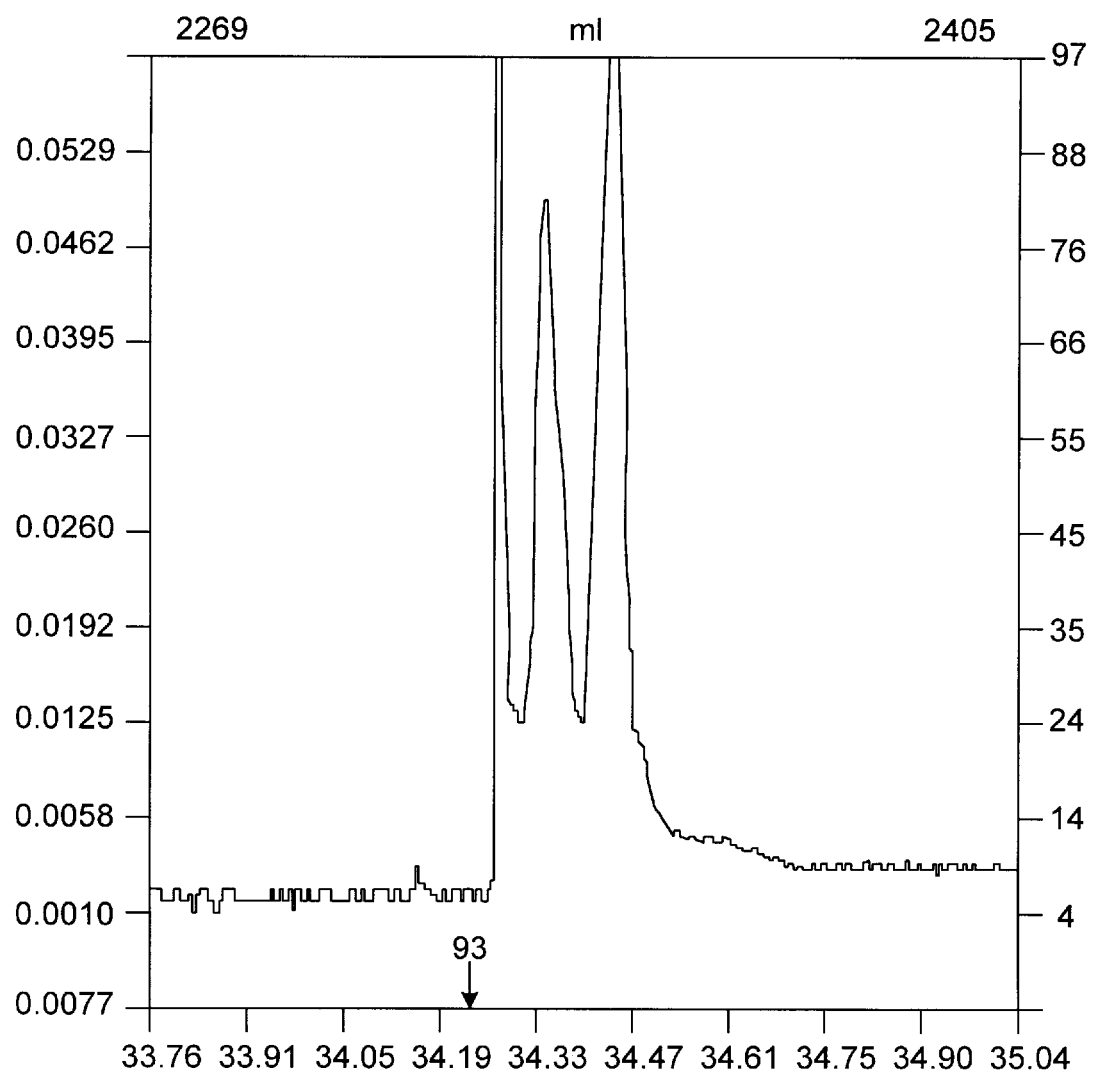
FIG. 13 is a chromatogram of preparative chromatography obtained in the separation of human transferrin and bovine serum albumin in a mixture thereof using the principles of the present invention.

The column was equilibrated with a 50 mM neutral pH tris buffer. A sample mixture of human transferrin (obtained from Sigma Chemical Co.) of molecular weight of about 80,000, and BSA (also obtained from Sigma Chemical Co.) of molecular weight of about 67,000, were dissolved in the buffer at a concentration of 2 mg/ml of each component, and the 5 mL injection loop was filled with the mixture. After equilibration of the column in the tris buffer, the sample was loaded onto the column at a flow rate of 120 mL/mn. After 5 seconds, the mobile phase was changed via a step gradient to 5% of the buffer with 2M NaCl. After an interval of an additional 7 seconds, the mobile phase was changed via a step gradient to 20% of the buffer/NaCl solution. Flow rate switching was performed manually on both instruments by changing the flow rates simultaneously to allow ionic separation of the protein solutes. The resulting chromatogram, as the ultra-violet trace of the elution at 280 nm, showing the resolution and peaks obtained during the total analysis time of approximately 15 seconds, is displayed in FIG. 13.

Figure 5:
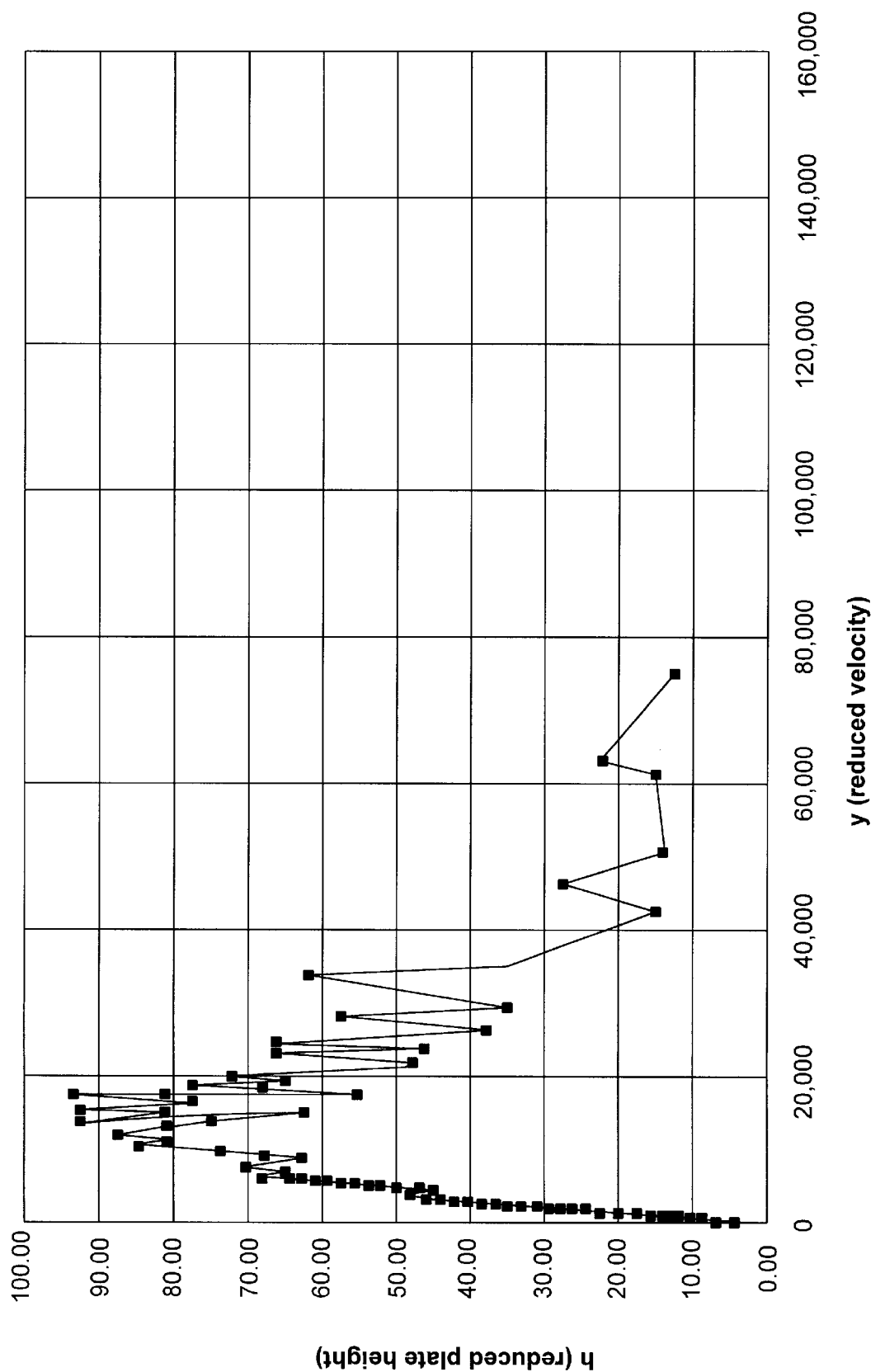
FIG. 5 is a graph of the measured data of a chromatographic column prepared according to the principles of the present invention with nominally 50$\mu$, unfunctionalized porous alumina particles, illustrating the efficiency of the column as a function of the fluid flow velocity through the column at various flow rates through the transition between laminar and turbulent flow, plotted in reduced coordinates.
Figure 6:
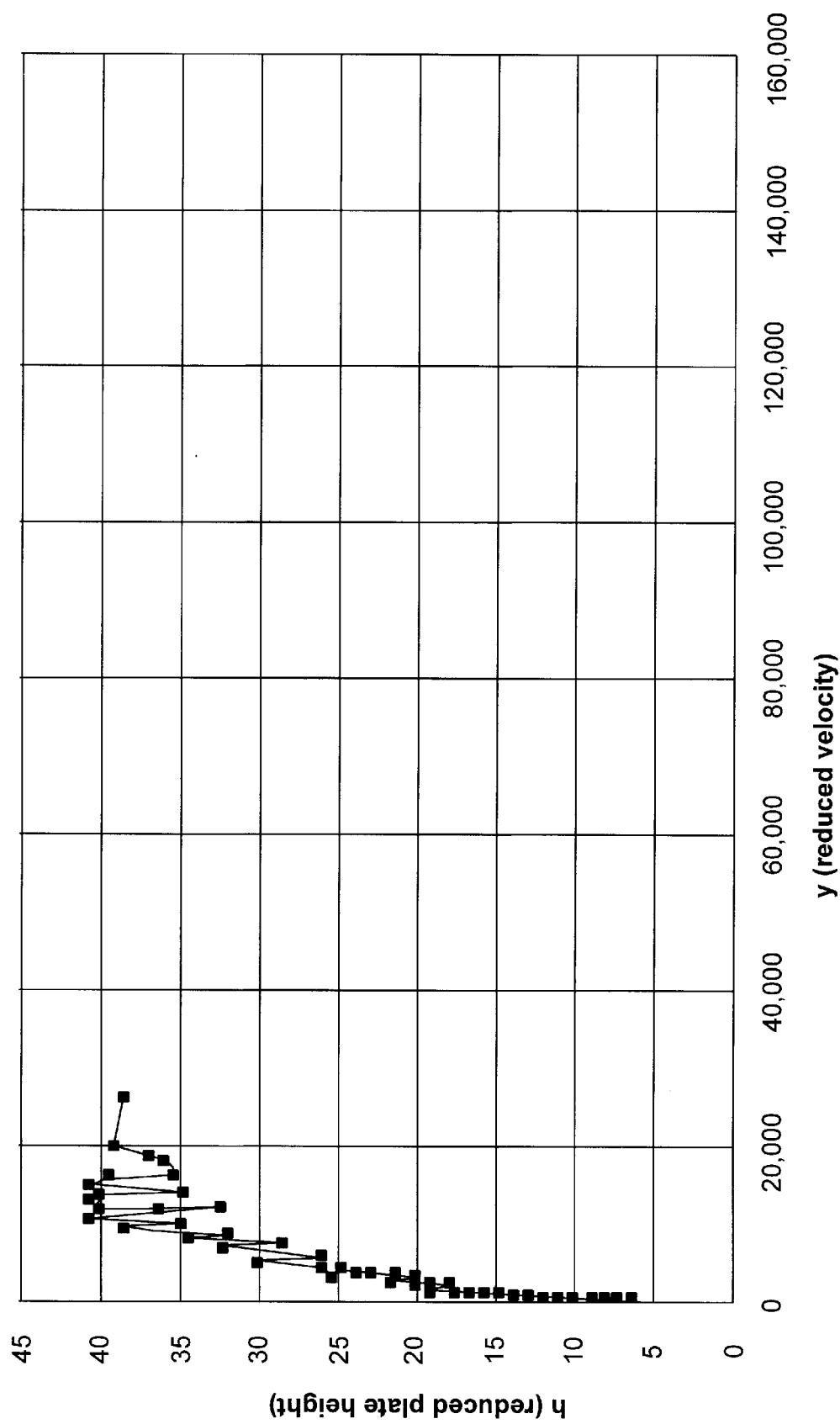
FIG. 6 is a plot similar to that of FIG. 5, illustrating the efficiency of a column of nominally 20$\mu$ particles plotted in reduced coordinates as in FIG. 5, as a function of the fluid flow velocity through the column, indicating that turbulence could not be attained with particles of that size, given the pressure constraints used in the Example graphed in FIG. 5.
Figure 7:
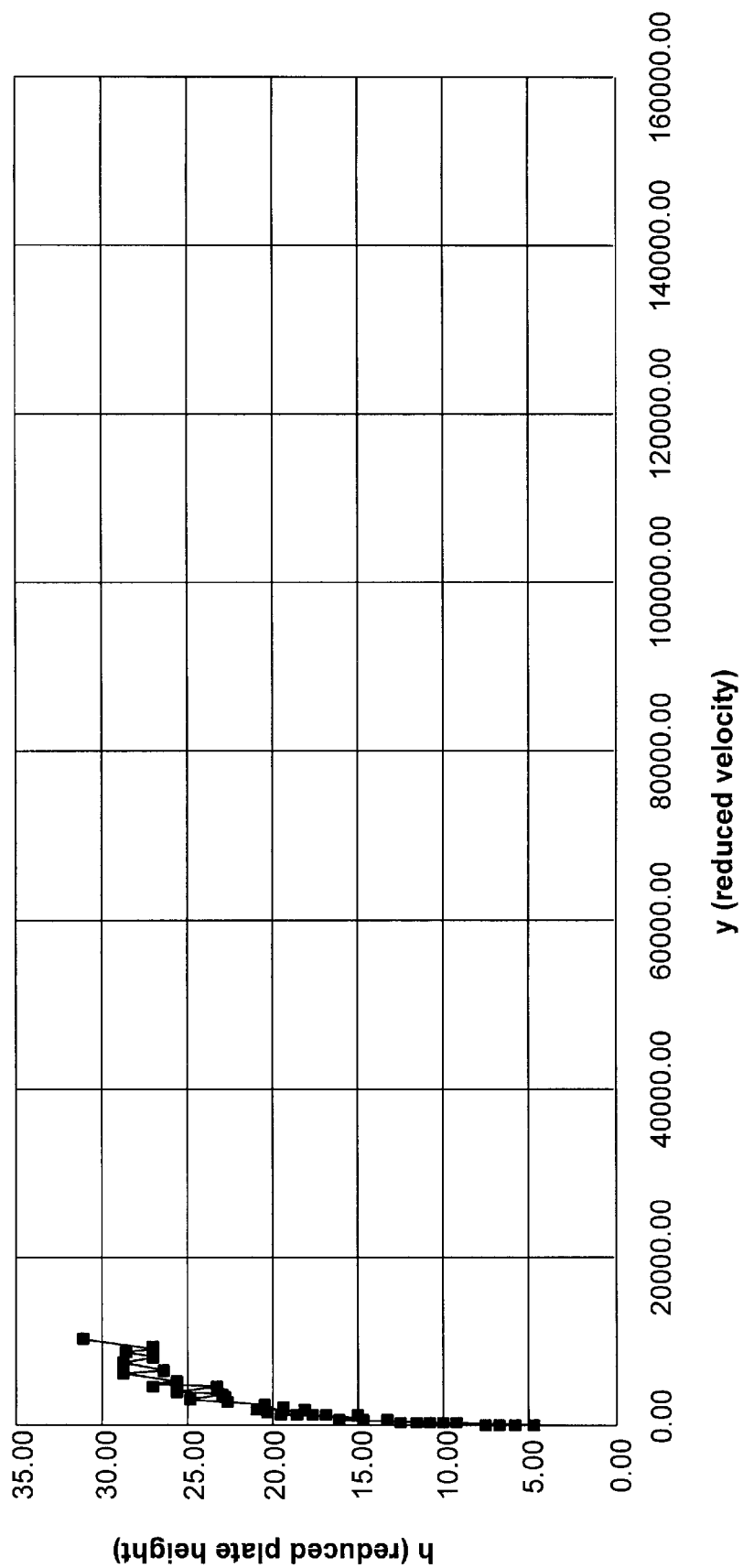
FIG. 7 is another plot similar to that of FIG. 5, based on an Example using nominally 10$\mu$ particles, clearly indicating that the turbulence could not be attained with particles of that size, given the pressure constraints used in the Example graphed in FIG. 5.

From the plots shown in the FIGS. 5–7 inclusive and the data in the Examples above, it is apparent that for the columns formed of the approximately 50 $\mu$m particles, the reduced plate height decreases above a reduced velocity value of about 5000, in contradistinction to the Van Deemter predictions. In columns of 50 $\mu$m particles that display such turbulent flow behavior, it is apparent from FIG. 5 that the reduced plate height returns to a minimum at a reduced velocity of approximately 40,000, and the time of analysis corresponding to this reduced velocity will be reduced by about the same amount, i.e. approximately $4\times10^4$. The columns formed of 10 $\mu$m and 20 $\mu$m particles do not show a like relationship of plate height to flow, but rather, as shown in the FIGS. 6 and 7, conform to the conventional relationship established by laminar flow.

When a desired solute may be present in very small concentrations in large volumes of liquid, the loading of a chromatographic column with the solute in preparation for separation can be a time-consuming and therefore expensive aspect of preparative chromatography. Because the present invention allows for relatively high speed flow through the column, not only can the time required for loading solute onto the column be markedly reduced, but it is believed that the turbulence engendered by such high speed flow enhances the loading of the solute molecules onto the derivatized surfaces in the pores of the particles in the column.

It will be also recognized that in purification of molecules, a major commercial concern is cost, and productivity can be defined as amount of material purified per unit time. Since the analysis time is decreased by the present invention by several orders of magnitude, it is reasonable to extend the same factor of savings to productivity as demonstrated particularly in Example 9. Since the dynamic capacity of the packed columns of the present invention is influenced by mass transfer considerations, this deduction appears quite relevant.

Another discovery, on which another embodiment of the present invention is based, also indicates that the prior art view of liquid chromatography is not accurate. For example, the Van Deemter equation, even in view of Giddings' coupling theory, predicts as noted earlier herein that the reduced plate height h value is not expected to be below about 2, even at high flow rates, and that the plate height is independent of the flow velocity of the mobile phase. It has now been found that, contrary to Van Deemter, the coupling coefficient (the a* term in Equ. 3) is not independent of flow rate and can assume values well below 1 by using turbulent flow velocities through a packed bed of large particles (e.g. at least 400 $\mu$m in average diameter). The significance of that discovery will be apparent from the following Example.

EXAMPLE 10

Another embodiment of apparatus of the present invention using a packed column was made employing apparatus similar to that shown in FIG. 2, in which column 20 was formed as a packed multiplicity of rigid, solid, preferably incompressible particles 22 having substantially uniform mean diameters with typically average diameters of several hundred $\mu$m. In this Example, column 20 was a 4.6×100 mm liquid chromatography column from Upchurch (Upchurch Scientific Co., Seattle, Wash.) with Upchurch 20 $\mu$m titanium frits, packed with particles of Davisil™ 636 Davison silica (W. R. Grace Co., Boca Raton, Fla.), having average diameters of about 500 $\mu$m as confirmed by optical microscopy. As in the earlier embodiment of particulate column 20 described hereinbefore, the surfaces of particles 22 were chromatographically active. Particles 22 had the attributes, other than of diameter, of any of the other particles earlier described herein.

Means such as metering pump 26 (Model N-P from Bran & Luebbe, Chicago, Ill.) were coupled to the proximal end of column 20, for flowing through at least a major portion of the interstitial volume of the column, a series of samples of a fluid mixture from an appropriate source such as reservoir 28. Each such sample was 40 $\mu$L of acetone diluted with HPLC grade water, injected by an appropriate loop injector 27 (Model 7125 from Rheodyne. L. P., Cotati, Cal.) at several experimental flow rates between about 80 and 140 mL/min. Detector means 31, (comprising Model UV-1000 detector from Thermo Separation Products, San Francisco, Calif., coupled to a Kipp & Zonen Model BD-112 recorder from Fisher Scientific, Pittsburg, Pa.) was disposed at the distal end of column 20.

The data resulting from operation of this latterly described liquid chromatography system is set forth in the following table which also shows the relation of the experimental flow rates, Q, in mL/min, (assuming a diffusion coefficient of $1.5\times10^{-5}$ cm$^2$/sec for acetone in water) to reduced velocities, $\upsilon$. The table indicates that at the typical values of $d_p$ and $\upsilon$ for such column 20, it has now been demonstrated that the reduced plate height h is inversely related to the velocity of the mobile phase, is not independent thereof or constant as believed in the prior art, and can reach values well below 1. Recovery, even of small molecules such as acetone, was extremely fast in that for each sample, the width and amplitude of peak detected by detector 31 indicated that there was substantially complete recovery of the injected acetone within less than 15 seconds per sample.

TABLE

| Q (mL/min) | $\mu$ (cm/s) | $\upsilon = \mu\, d_p/D_M$ | N = 5.54 $(t_R w_{1/2})^2$ | H ($\mu$m) | h |
|---|---|---|---|---|---|
| 80 | 11.4 | 38,000 | 112 | 893 | 1.78 |
| 100 | 14.3 | 48,000 | 182 | 549 | 1.10 |
| 120 | 17.2 | 57,000 | 220 | 454 | 0.91 |
| 140 | 20.0 | 67,000 | 244 | 410 | 0.82 | where
$\mu$=the average mobile phase linear velocity,
$\upsilon$=the reduced linear velocity;

N=the number of theoretical plates;

H=the plate height; and h=the reduced plate height.

Figure 14:
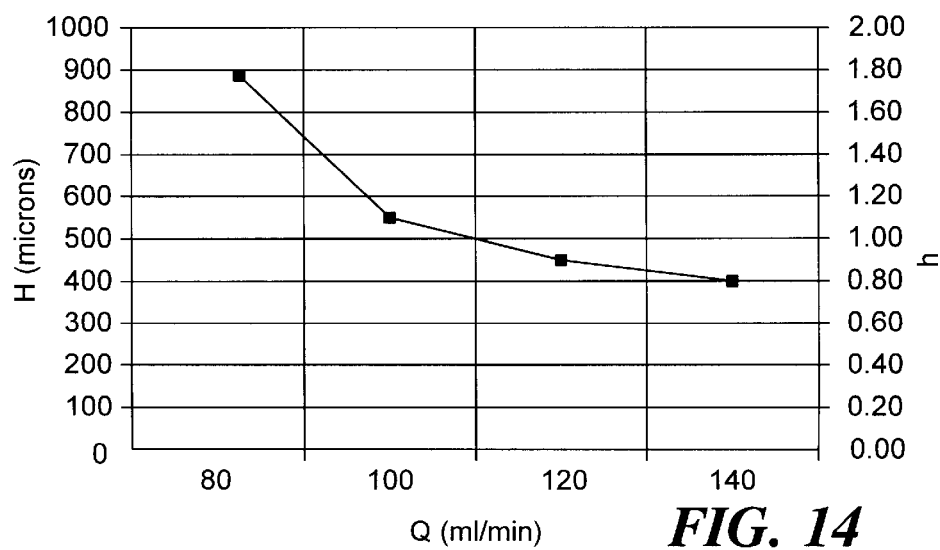
FIG. 14 is a plot of data obtained from injecting at several different very high flow rates, samples of acetone in water into an HPLC column using a packed bed of very large particles.

A plot of the values of the flow rate, Q in mL/min, against the measured value of plate height, H in μm, is shown in FIG. 14. From the data provided by Example 10 it is apparent that preparative chromatography using apparatus as described in connection therewith can result in extremely high speed, high capacity separation even for molecules having molecular weights well below 100.

As illustrated hereinbefore, mass transfer is enhanced by turbulent flow and it is now believed that the mechanism involved is the consequent reduced access to surface area binding sites on the chromatographic particles. Accordingly, if the postulated mechanism is correct, then non-specific binding should be correspondingly reduced. Non-specific binding, as that term is used herein, is intended to refer to the phenomenon in chromatography in which a molecule of sample, trapped at a surface binding site on a chromatographic particle resists subsequent displacement by elution, or cannot be removed by elution. In order to establish the truth of this hypothesis, the following study was undertaken:

EXAMPLE 11

A pair of 0.46×10 cm HPLC columns were prepared as described above in Example 6, and evaluated with instrumentation as described in Example 9. A sample mixture of BSA (Sigma Chemical Co.) was prepared by dissolution at a concentration of 60 mg/mL in the mobile phase formed of tris buffer at pH 8.62 with 2M NaCl. After equilibration of the columns with buffer, a plurality of 10 μL injections of the sample were made consecutively into each column at an average flow rate at reduced velocities greater than about 5000. Recovery of the sample was measured as a function of area. Each column was first tested at an elution flow rate of the mobile phase of 30 mL/min which corresponds, for this sample and particle size in the column, to a reduced velocity in excess of 30,000. Once saturation at these high flow rates was achieved, the study continued using the same columns, but at a flow rate of 1 mL/min corresponding to a more traditional regime of laminar flow in accordance with the teachings enunciated in the Van Deemter relationship.

Figure 15:
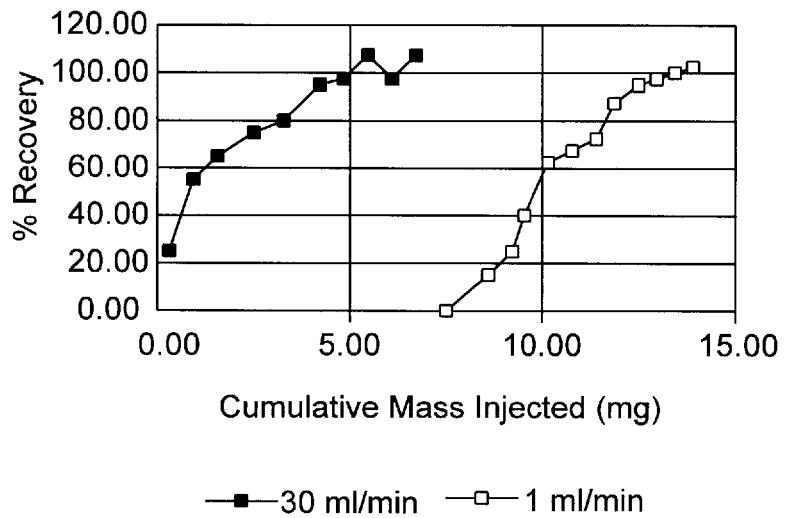
FIG. 15 is a plot of data obtained from injecting a sequence of the same samples as into an HPLC column and eluting the samples first at a turbulent flow rate, followed by a laminar flow rate, to illustrate non-specific binding in terms of recovery of the sample as a function of the cumulative mass of sample solution.
Figure 16:
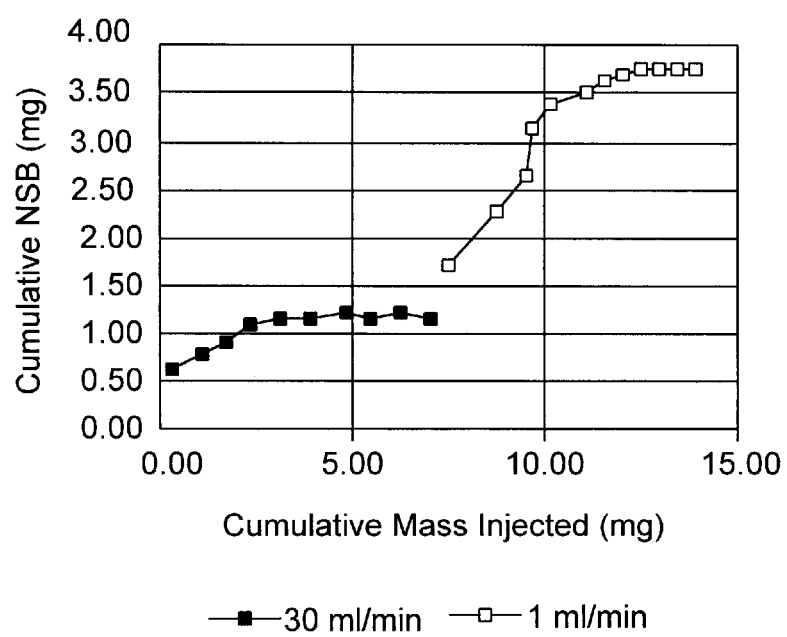
FIG. 16 is a plot of data obtained from injecting a sequence of the same samples into an HPLC column and eluting the samples first at a turbulent flow rate, followed by a laminar flow rate, to illustrate non-specific binding in terms of cumulative non-specific binding of the sample as a function of the cumulative mass of sample solution.

The resulting data are represented graphically in FIGS. 15 and 16. It will be recognized that under the foregoing conditions and the nature of the mobile phase employed, the BSA in the sample is generally unretained, but is known to have non-specific binding interactions, presumably with the underlying alumina support. It will be appreciated that non-specific binding can present a serious problem in HPLC inasmuch as inorganic substrates tend to "eat" finite amounts of sample which may be present in only minute quantities and/or be very valuable. As shown in FIG. 15, under turbulent flow conditions the percentage of sample recovered reached 100% by the time the cumulative mass of the injected sample solution had reached 5 mg. Under a laminar flow regime, 100% recovery was not achieved until the cumulative mass of sample solution injected had reached about 13 mg, indicating that considerably more non-specific binding of sample occurred under laminar flow conditions than occurred under conditions of turbulent flow. FIG. 16 simply restates the data in terms of cumulative amount of non-specific binding that occurred rather than as recovery, showing that, for the columns employed, the actual mass of BSA non-specifically bound plateaued or saturated at about 1.2 mg for turbulent flow conditions, but did not plateau for laminar flow until about 3.8 mg of BSA had been non-specifically bound. It is therefore apparent that by employing turbulent flow conditions in HPLC, losses due to non-specific binding can be substantially minimized. To that end, in chromatographic columns in which a solute in a sample introduced into the column may tend to become non-specifically bound to the column particles, the teachings of the present invention are useful in reducing such non-specific binding by providing means for injecting the sample into the column and means for flowing, substantially immediately after the sample injection, eluant fluid into the column, both the injection and the flow of eluant fluid being established at an average reduced velocity greater than about 5000.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. Chromatography apparatus comprising, in combination, a chromatographic body formed as a substantially uniformly distributed multiplicity of rigid, solid, porous particles with chromatographically active surfaces, said particles having average diameters of greater than about 30 μm, the interstitial volume between said particles being not less than about 45% of the total volume of said column; and means for loading said surfaces with at least one solute that is reactive with said surfaces, by flowing a liquid mixture containing said solute through said body at a velocity sufficient to induce flow of said mixture within at least a substantial portion of said interstitial volume at a reduced velocity greater than about 5,000.

2. Chromatography apparatus as set forth in claim 1 wherein said mean diameters of said particles are substantially uniform.

3. Chromatography apparatus as set forth in claim 1 wherein said interstitial volume comprises a multiplicity of interstitial channels between said particles, at least the majority of said channels having mean cross-section dimensions substantially not less than about 5 μm.

4. Chromatography apparatus as set forth in claim 1 wherein said particles are coated with stationary phase layers so as to render said surfaces chromatographically active.

5. Chromatography apparatus as set forth in claim 1 wherein said particles are substantially incompressible so as to substantially resist plastic deformation at packing pressures up to about $1 \times 10^4$ psi.

6. Chromatography apparatus as set forth in claim 1 wherein said particles are formed from one or more of alumina, silica, titania, vanadia, zirconia and carbon.

7. Chromatography apparatus as set forth in claim 1 wherein the pores in said particles have mean diameters lying within the range of from about 60 Å to about 5,000 Å.

8. Chromatography apparatus as set forth in claim 1 wherein said particles are packed together under a pressure of substantially not less than $5 \times 10^3$ psi.

9. Chromatography apparatus as set forth in claim 1 including means for eluting loaded solute from said body by flowing an eluant fluid through said body at a velocity sufficient to induce flow of said eluant fluid within at least a substantial portion of said interstitial volume at a reduced velocity greater than about 5,000.

10. Chromatography apparatus as set forth in claim 1 including means for eluting loaded solute from said body by flowing an eluant fluid through said interstitial volume at a velocity selected such that band spreading of solute eluted by said eluant fluid from said body is an inverse function of the Reynolds number for the eluant fluid flow and is a direct function of the magnitude of the diffusion coefficient of said solute in said eluant fluid.

11. Chromatography apparatus as set forth in claim 1 including means for eluting loaded solute from said flowing an eluant fluid through said interstitial volume at a velocity selected such that band spreading of solute eluted by said eluant fluid from said body decreases with increasing Reynolds number of the eluant flow.

12. Chromatography apparatus as set forth in claim 1 including means for eluting loaded solute rom said body by flowing eluant fluid through said interstitial volume at a velocity selected such that band spreading of solute eluted by said eluant fluid from said body is a direct function of the magnitude of the diffusion coefficient of said solute in said eluant fluid.

13. Chromatography apparatus comprising, in combination,
   a chromatographic column formed as a substantially uniformly distributed, packed multiplicity of rigid, solid, porous particles with chromatographically active surfaces, said particle having substantially uniform average diameters of not less than about 500 $\mu$m, and
   means for loading said surfaces with at least one solute that is reactive with said surfaces, by flowing a liquid mixture containing said solute through said column at a velocity sufficient to induce flow of said mixture within at least a substantial portion of the interstitial volume between said particles at a reduced velocity greater than about 50,000.

14. Chromatography apparatus as set forth in claim 13 including means for eluting loaded solute from said column by flowing an eluant fluid through said column at a reduced velocity value of at least about 50,000.

15. In chromatography apparatus including a chromatographic column formed as a bed of a packed multiplicity of rigid solid particles having substantially uniform mean diameters of not less than about 30 $\mu$m, the surfaces of said particles being chromatographically active and wherein a solute introduced into said bed tends to become non-specifically bound to said particles, the improvement including means for injecting a liquid mixture comprising said solute into said column at a reduced velocity greater than about 5,000 so as to load said particles with said solute; and means for eluting the loaded solute from said particles by flowing eluant fluid through said column at an average reduced velocity greater than about 5000.

16. A chromatographic column comprising, in combination,
   a container packed with a substantially uniformly distributed multiplicity of rigid, solid, porous particles with chromatographically active surfaces, said particle having substantially uniform average diameters in the range between about 30 to about 500 $\mu$m, the interstitial volume between said particles being greater than about 45% of the total volume of said body, said volume being formed of a multiplicity of interstitial channels between said particles, at least a majority of said channels having mean cross-section dimensions substantially not less than about 5 $\mu$m.

17. A chromatographic column as set forth in claim 16 wherein said particles are coated with stationary phase layers so as to render said surfaces chromatographically active.

18. A chromatographic column as set forth in claim 16 wherein said particles are substantially incompressible so as to substantially resist plastic deformation at packing pressures up to about $1 \times 10^4$ psi.

19. A chromatographic column as set forth in claim 16 wherein said particles are formed from one or more of alumina, silica, titania, vanadia, zirconia and carbon.

20. A chromatographic column as set forth in claim 16 wherein the pores in said particles have mean diameters lying within the range of from about 60 Å to about 5,000 Å.

21. A chromatographic column as set forth in claim 16 wherein said particles are packed together under a pressure of substantially not less than $5 \times 10^3$ psi.

22. A chromatographic column apparatus as set forth in claim 16 wherein said particles are selected to have diameters of at least about 500 $\mu$m.

* * * * *